United States Patent [19]

McClure et al.

[11] Patent Number: 5,350,407
[45] Date of Patent: Sep. 27, 1994

[54] IMPLANTABLE STIMULATOR HAVING QUIESCENT AND ACTIVE MODES OF OPERATION

[75] Inventors: Lawrence C. McClure, Parker; Kent E. Samuelson; Daniel L. Hansen, both of Aurora, all of Colo.

[73] Assignee: Telectronics Pacing Systems, Inc., Englewood, Colo.

[21] Appl. No.: 998,962

[22] Filed: Dec. 30, 1992

[51] Int. Cl.⁵ .......................................... A61N 1/362
[52] U.S. Cl. .................................................. 607/16
[58] Field of Search .......................... 607/9, 16, 27, 30

[56] References Cited

U.S. PATENT DOCUMENTS

| | | | |
|---|---|---|---|
| 3,241,556 | 3/1966 | Zacouto | 607/9 |
| 4,404,972 | 9/1983 | Gordon et al. | 128/419 PG |
| 4,605,007 | 8/1988 | Heraly | 607/27 |
| 4,705,042 | 11/1987 | Giurtino | 607/27 |
| 4,830,005 | 5/1989 | Woskow | 607/27 |
| 5,022,395 | 6/1991 | Russie | 607/16 |

FOREIGN PATENT DOCUMENTS

| | | | |
|---|---|---|---|
| 0077845 | 5/1983 | European Pat. Off. | 607/16 |
| 3218733 | 12/1982 | Fed. Rep. of Germany | 607/16 |
| 0246254 | 6/1987 | Fed. Rep. of Germany | 607/9 |
| 1267046 | 3/1972 | United Kingdom | 607/9 |

*Primary Examiner*—William E. Kamm
*Attorney, Agent, or Firm*—Gottlieb, Rackman & Resisman

[57] ABSTRACT

A method and apparatus for selectively controlling an oscillator-driven implantable stimulator to operate either in a quiescent state, in response to a command from an external communicating device, or in an active state in response either to removal of an activation pin or to an activating command from an external communicating device. Upon completion of manufacture of the stimulator, and before being placed on a shelf to await implantation in a patient, the activation pin is inserted into the stimulator and the external communicating device is triggered to send a deactivating command to the stimulator. The stimulator responds by generally disabling current sources to stimulator circuits, while maintaining current sources to a wake up circuit of the stimulator that is associated with communication operations. The stimulator is activated by subsequently transmitting an activating command from an external communicating device to the implantable stimulator, or by removing the activation pin.

35 Claims, 15 Drawing Sheets

IMPLANTABLE STIMULATOR HAVING QUIESCENT AND ACTIVE MODES OF OPERATION

This invention relates to battery-powered implantable cardiac stimulators and, more particularly, to implantable cardiac stimulators that extend the useful life of the battery and significantly increase shelf life by turning off power to nonessential circuits when they are not required, while activating the circuits into a known appropriate state when necessary.

BACKGROUND OF THE INVENTION

It is common for implantable cardiac stimulators, such as pacemakers and defibrillators, to be implemented in the form of various circuits under the control of a microprocessor. The functions these circuits perform include pulse generation, cardiac electrical signal sensing, performance of various diagnostic and physiological measurements and communication between the implanted stimulator and an external communicating device, commonly called a programmer. One of the problems with cardiac stimulator implementations is that they require large current consumptions and, therefore, high battery drains, which tend to result in short product lives, large product sizes or a combination of these two disadvantageous conditions.

One early current-saving improvement to microprocessor-controlled pacemakers was the implemention of "wakeup" control. P. L. Gordon et al., in U.S. Pat. No. 4,404,972, entitled "Implantable Device with Microprocessor Control", issued on Sep. 20, 1983, disclose a pacemaker in which its controlling microprocessor operates only in response to various external physiological events and internal timer events. These physiological events and timer events act upon internal logic circuits which, in turn, generate wakeup signals acting upon the microprocessor. The microprocessor enables and disables these internal logic circuits to determine which wakeups may activate the microprocessor. The microprocessor responds to a wakeup signal from an internal logic circuit by becoming active and performing a wakeup routine. At the end of this routine, the microprocessor determines which set of wakeup events are active and which are inactive. Then the microprocessor sends control signals to activate and deactivate the appropriate internal logic components. In the final step of the wakeup routine, the microprocessor deactivates itself.

Battery operated microprocessors use complementary metal-oxide-silicon (CMOS) circuits to reduce power consumption. However, to take full advantage of CMOS circuits, the circuits must not be clocked when their usage is not required. CMOS circuits provide for very low standby power consumption when they are not being clocked. Thus, it is known that the useful life of a battery in a microprocessor-controlled implantable device may be extended by turning off power to nonessential circuits at certain time periods during which such circuits are not required.

Present day pacemakers begin pacing immediately upon manufacture and continue to pace at an amplitude and rate which are deemed to be safe for nearly all cardiac patients. Pacemakers are not turned off between the time of their manufacture and the time of their implantation because of the risk of implanting them while they are in a turned-off condition. A pacemaker may, thus, sit on a shelf for months while it is continuously pacing and wasting power.

When using a battery-powered control system, such as that within a pacemaker, it is desirable to extend the life of the power source without jeopardizing the functioning of the control system.

It is desirable to be able to turn off an implantable stimulator after it is manufactured while assuring that it will be activated into a known state before it is implanted.

It is, therefore, a primary object of the present invention to provide a method and apparatus for deactivating a stimulator into a quiescent state, during which only essential functions of communication and memory maintenance are enabled, and for reactivating the stimulator into a known active state.

It is also an object of the present invention to provide, in an implantable device powered by a limited capacity electrical power source, a lower level of power consumption to thereby extend the life of the power source and expand the shelf life of the device.

It is an additional object of the present invention to lower the level of power consumption and extend the life of the power source without altering stimulator functionality or integrity.

It is another object of the present invention to provide for a communication link between an implantable stimulator and an external device which always remains operable even though the stimulator may be placed in a quiescent state.

It is further object of the present invention to maintain any information stored in volatile memory in an implantable stimulator, even though the stimulator may be placed in a quiescent state.

It is yet another object of the present invention to provide a method and apparatus which distinguish a cardiac stimulation system reset condition caused by the quiescent state from a system reset condition caused by an error.

It is a still further object of the present invention to provide a method and apparatus for placing a cardiac stimulator in a quiescent state, which method and apparatus are fool-proof and prevent a stimulator from being implanted in its quiescent state.

Further objects and advantages of the invention will become apparent as the following description proceeds.

SUMMARY OF THE INVENTION

Briefly stated, the stimulator of the present invention suspends all non-essential current sources and bias current generators while retaining the current source to the oscillator, disables all non-essential wakeup signals while retaining wakeup signals which drive communication operations, and disables error detection circuits which would otherwise generate error notifications due to the quiescent state of the stimulator.

In accordance with the principles of one embodiment of the invention, a method is provided for selectively controlling an oscillator-driven implantable cardiac stimulator to operate either in a quiescent state or in an active state in response to commands from an external communicating device. Upon completion of manufacture, and before being placed on a shelf to await implantation in a patient, the external communicating device sends a deactivating command to the implantable stimulator. The stimulator responds: (1) by disabling power to stimulator circuits in general, while maintaining power to the oscillator, and (2) by disabling operations of the stimulator in general, while maintaining operations associated with communication. Later, the stimulator may be activated by subsequently transmitting an activating command to the implantable stimulator. In response to the activating command, the stimulator enables the previously disabled operations and enables power to the previously unpowered stimulator circuits.

In accordance with this first embodiment of the invention, an implantable cardiac stimulator is adapted to operate either in a quiescent state or in an active state in response to commands from an external communicating device. The stimulator includes an oscillator to provide timing signals to drive stimulator functions and a communication circuit for communicating with the external communicating device. The stimulator further includes two circuits, both of which respond to deactivating and activating commands from the external communicating device. The first circuit generally disables power to stimulator circuits while continuing to enable power to the oscillator in response to the deactivating command, and enables power to all stimulator circuits in response to the activating command. The second circuit generally disables operations of the stimulator while continuing to enable operations associated with the communication circuit in response to the deactivating command, and enables operations of all stimulator circuits in response to the activating command.

In accordance with the principles of a second embodiment of the invention, a method is provided for selectively controlling an oscillator-driven implantable cardiac stimulator to operate either in a quiescent state in response to a command from an external communicating device or in an active state in response to removal of an activation pin. The stimulator includes an aperture or socket adapted to accept either a stimulation lead or an activation pin, and a circuit that is adapted to detect removal of an inserted activation pin. Upon completion of manufacture, and before being placed on a shelf to await implantation in a patient, the activating pin is inserted into the stimulator socket. Then, the external communicating device sends a deactivating command to the implantable stimulator. The stimulator responds by generally disabling power to stimulator circuits while maintaining power to the oscillator, and generally disabling operations of the stimulator while maintaining the operations of the stimulator associated with communication operations. Later, the stimulator may be activated by removing the activation pin from the stimulator aperture. In response to the removal of the activating pin, the stimulator enables the previously disabled operations and enables power to the previously unpowered stimulator circuits.

In accordance with this second embodiment of the invention, an implantable cardiac stimulator is adapted to operate either in a quiescent state in response to commands from an external communicating device or in an active state in response to removal of an activation pin. The stimulator includes an oscillator to provide timing signals to drive stimulator functions, an aperture or socket adapted to receive a stimulation lead and capable of receiving the activation pin, a circuit adapted to detect removal of the inserted activation pin and a communication circuit for communicating with the external communicating device. The stimulator includes two circuits, both of which respond to deactivating commands from the external communicating device and respond to removal of the activation pin. The first circuit generally disables power to stimulator circuits while continuing to enable power to the oscillator in response to the deactivating command, and enables power to all stimulator circuits in response to removal of the activation pin. The second circuit generally disables operations of the stimulator while continuing to enable operations associated with the communication circuit in response to the deactivating command, and enables operations of all stimulator circuits in response to removal of the activation pin.

In accordance with the principles of a third embodiment of the invention, a method is provided for selectively controlling an oscillator-driven implantable cardiac stimulator to operate either in a quiescent state or in an active state in response to a command from an external communicating device. The stimulator includes at least one storage register, a power supply for regulating current sources to stimulator circuits, an oscillator for providing timing signals to stimulator circuits, and a wakeup circuit for notifying the stimulator of internal and external wakeup events, with these wakeup events being capable of individual enabling and disabling. Upon completion of manufacture, and before being placed on a shelf to await implantation in a patient, the external communicating device sends a deactivating command to the implantable stimulator. The stimulator responds by storing a representation of the transmitted deactivating command in a storage register, which disables current sources to stimulator circuits in general while maintaining current sources to the oscillator, and which disables the wakeup circuits of the stimulator in general while maintaining activity of the wakeup circuits associated with communication operations. The external communicating device may subsequently interrogate the storage register to determine whether the stimulator is in a deactivated state and to program the deactivated stimulator. The stimulator may be activated by subsequently transmitting an activating command from an external communicating device to the implantable stimulator. In response to the activating command, the stimulator enables the previously disabled wakeup circuit and enables current sources to the previously disabled stimulator circuits.

In accordance with this third embodiment of the invention, an implantable cardiac stimulator is adapted to operate either in a quiescent state in response to commands from an external communicating device, or in an active state either in response to an activating command from the communicating device or in response to removal of an activation pin. The stimulator includes an oscillator to provide timing signals to drive stimulator functions, an aperture or socket adapted to receive a stimulation lead and capable of receiving the activation pin, a circuit adapted to detect removal of the inserted activation pin, at least one storage register, a power supply for regulating current sources to stimulator circuits, a wakeup circuit for notifying the stimulator of internal and external wakeup events and for individually enabling and disabling these wakeup events, means for storing a representation of a transmitted deactivating command from the external communicating device in a storage register, and a communication circuit for communicating with the external communicating device. The stimulator further includes means responsive to a deactivating command from the external communicating device for controlling the power supply to generally disable current sources to stimulator circuits while continuing to enable the current source to the oscillator. The stimulator still further includes means, responsive to a deactivating command from the external communicating device, for controlling the wakeup circuit to generally disable wakeup events while continuing to enable the wakeup events associated with the communication circuit. In addition the stimulator includes means for interrogating the deactivating command storage register to determine whether the stimulator is in a deactivated state, and means for programming the deactivated stimulator. The stimulator also includes two circuits, both of which are responsive either to an activating command from an external communicating device or to removal of the activation pin. One circuit controls the wakeup circuits to enable wakeup events. A second circuit controls the power supply to enable current sources to stimulator circuits.

BRIEF DESCRIPTION OF THE DRAWINGS

While the specification concludes with claims particularly pointing out and distinctly claiming the subject matter of the invention, it is believed that the invention will be better understood upon consideration of the following detailed description, taken in conjunction with the accompanying drawings, in which:

DETAILED DESCRIPTION OF THE INVENTION

Figure 1:
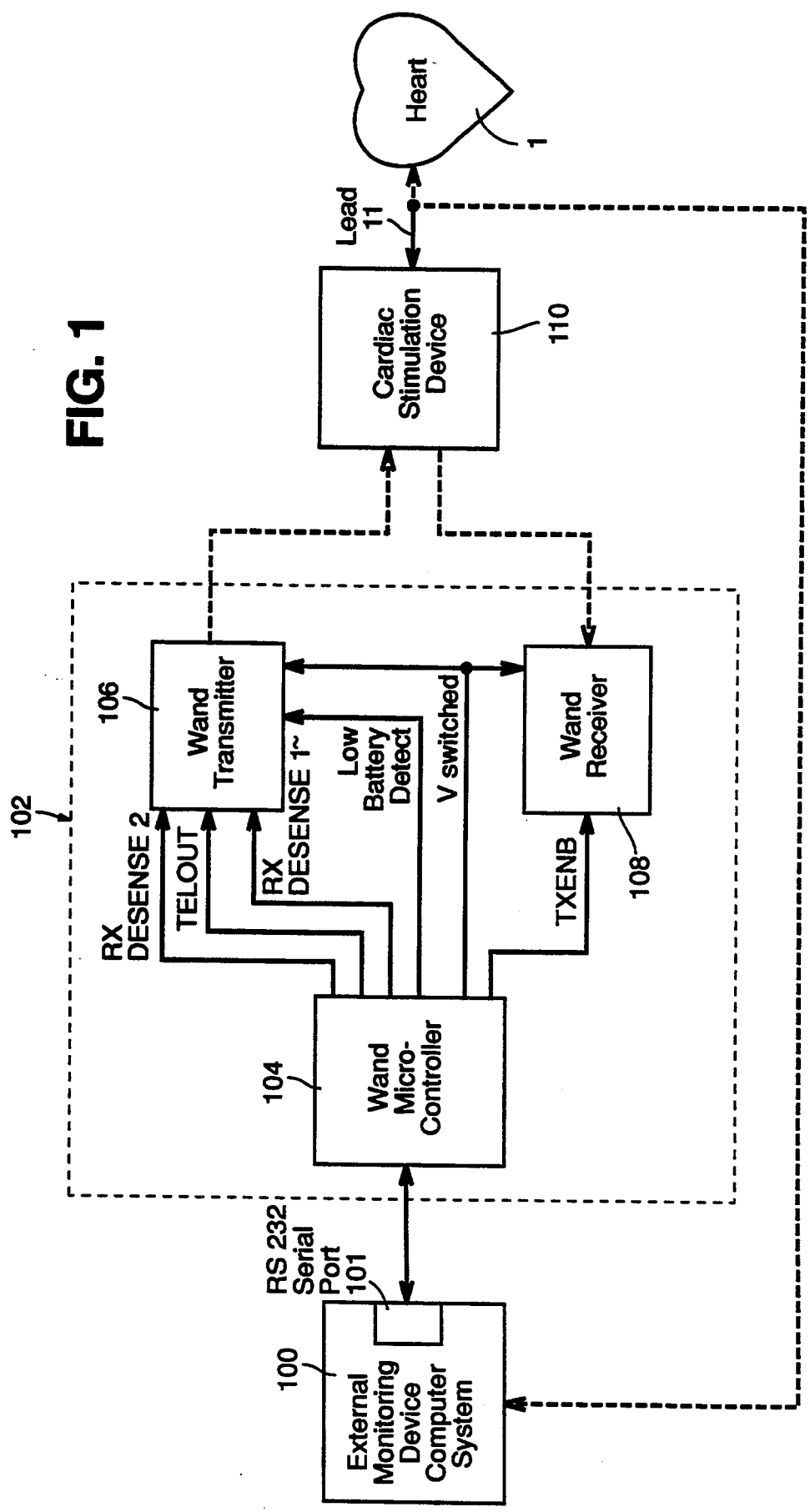
FIG. 1 is a high-level system block diagram showing the components of the present invention.

FIG. 1 is a high-level system block diagram showing the component blocks of the present invention, in which an external monitoring device computer system or programmer 100 communicates with an implantable cardiac stimulation device or stimulator 110 by means of a programming wand 102, which provides a telemetric communication link therebetween. The stimulator 110 employs a bipolar lead 11, making an electrical connection to a heart 1 to stimulate the heart and to detect physiological signals from the heart. The programming wand 102 allows communication between the stimulator 110 and the external monitoring device computer system 100 for monitoring and analysis of the physiological functionality of the heart 1.

The external monitoring device computer system 100 may be a standard personal computer (PC) system, which executes the programmer software as is known in the art of cardiac pacemakers, in addition to performing new functions provided by the present invention.

The programming wand 102 of FIG. 1 provides a communications interface between the external monitoring device computer system 100 and the implantable cardiac stimulation device 110. Bidirectional communication between the programming wand 102 and the computer system 100 takes place using a high speed RS-232 serial port 101. A wand microcontroller 104, within the programming wand 102, receives data and control signal information from the computer system 100 and drives a wand transmitter 106 to send this information to a cardiac stimulation device 110. This control information may be in the form of a request for the cardiac stimulation device 110 to transmit data such as operational parameters, intracardiac electrograms, physiological signals, information compiled from biological signals, and diagnostic test data back to the computer system 100 for analysis and display. As the stimulator 110 complies with this request for information, the programming wand 102 receives, amplifies, filters and decodes telemetry signals sent by the stimulator 110 and advances these signals to the external monitoring device computer system 100.

Physically, the programming wand 102 is a "mouse"-shaped housing (not shown) which contains circuitry for the wand microcontroller 104, the wand transmitter 106 and a wand receiver 108. The housing is connected by a coil cord (not shown) to a molded connector assembly (not shown) which connects to the RS-232 serial port 101 of the computer system 100. The connector assembly also contains a 9 volt battery (not shown), the power source for the programing wand 102.

The programming wand 102 includes functional circuits for the wand microcontroller 104, the wand transmitter and the wand receiver 108.

Figure 2:
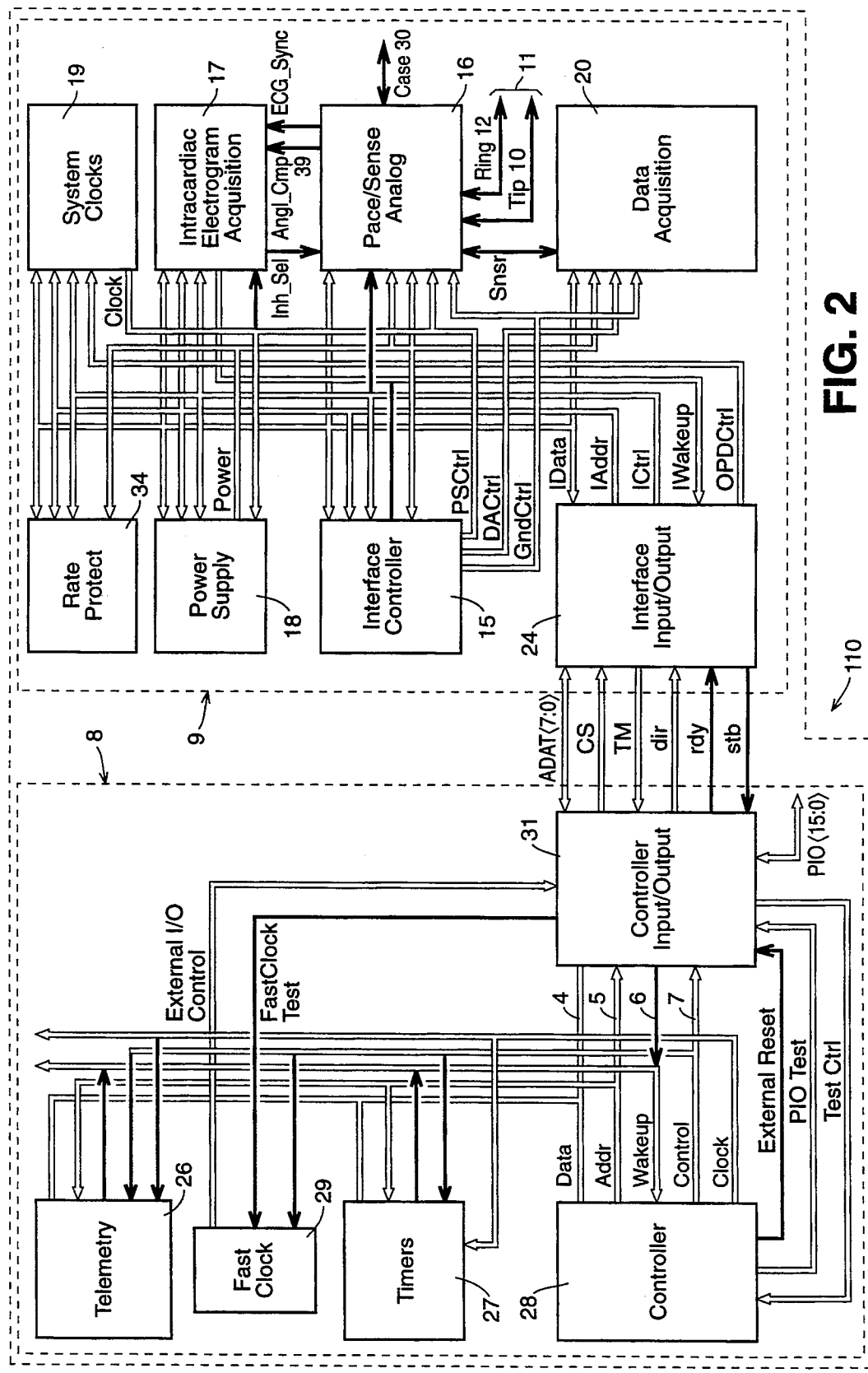
FIG. 2 is a high-level block schematic of an implantable cardiac stimulation device or stimulator shown in FIG. 1.

The drawing of FIG. 2 is a high-level block schematic depicting the implantable cardiac stimulation device 110. A tip electrode 10 and a ring electrode 12, respectively, are those found in a conventional bipolar lead 11. The fundamental requirements for a cardiac stimulation device include the ability to generate and deliver, at selected intervals, electrical stimulation pulses of varying amplitudes and forms.

All implantable stimulator 110 logic is under the control of controller 28 (which may include a microprocessor), which controls all of the other blocks of FIG. 2. In the preferred embodiment of the invention, the controller 28 is a firmware-based microcontroller designed specifically for implantable applications. The controller 28 fetches micro-coded instructions from control store ROM (not shown) located internal to the controller, executes these instructions and sequences to the next instruction. Control store ROM contains the executable control program instructions performed by the controller 28. The controller is inactive when no operations are pending, activates upon a "wakeup" command and executes other logic functions which are necessary in an algorithm-based implantable device. Logic blocks, such as a telemetry block 26, a timers 27 block, a pace/sense analog circuit 26, an interface controller 15 and an intracardiac electrogram acquisition circuit 17 generate wakeup commands which activate operations of the controller 28.

Input signals to the controller 28 are a system reset signal, a 32 kHz clock signal, four wakeup lines from external subsystems and various execution clock signals. Output signals which are provided by the controller 28 to other subsystems are a system-wide reset signal, various clock subharmonic signals, and digital data 4, address 5, and control 7 bus signals.

Telemetry block 26 is a conventional communications circuit in modern implanted cardiac stimulation devices, such as pacemakers, defibrillators and antitachycardia pacemakers. By means of an antenna (not shown), the telemetry block 26 allows for bidirectional communication of information between an external (not implanted) programming device, such as the external monitoring device computer system 100, and the implantable stimulator 110. Communication permits both an adjustment of the data acquisition parameters from the external programmer, and transmission of information from the implanted device to the external device. The information transmitted from the implanted stimulator 110 to the external programmer 100 may include accumulated data and a signal representative of the instantaneous sensed intracardiac electrogram.

The implantable stimulator 110 uses timers 27 to measure various time intervals and provide timing control for circuit operations, physiological stimulation or real time events. The timers 27 block includes circuits to provide three independent interval timers-timer 0, timer 1 and timer 2 (not shown). The controller 28 writes timing initilization and duration information to timers 27. The timers 27 respond by generating wake up signals T0, T1 and T2, via wakeup lines 6, to the controller 28, after respective time intervals for timer 0, timer 1 or timer 2 expire. The controller 28 determines the duration of these time intervals by writing initialization and duration codes to control registers (not shown) within the timers 27. The controller employs timer wake ups to govern the timing of cardiac cycles, as well as to time short-term intervals for miscellaneous operations. The controller uses timer wake up signals to control a real-time clock function that determines the length of time since manufacture of the device and initiates long-term housekeeping functions.

A controller input/output block 31 supports external input and output functions so that a processor subsystem 8, which includes the controller 28, the timers 27, the telemetry block 26 and a fast clock 29 can read and write data to and from external data lines to various source and destination subsystems, such as an interface subsystem 9 of FIG. 2. The controller input/output block 31 is an interface to external devices that supports read and write operations to control/status and data registers in such external devices. Controller input/output block 31 provides for three modes of communication: memory-mapped input and output, a parallel input and output, and test modes.

Interface input/output block 24 provides an interface between the controller input/output block 31 of the processor subsystem 8 and an interface subsystem 9 which includes the interface controller 15, the pace/-sense analog circuit 16, a data acquisition circuit 20, the intracardiac electrogram acquisition circuit 17, a rate protection circuit 34, system clocks 19 (which supply stable crystal-controlled clock signals for numerous timing functions within the processor 8 and the interface 9 subsystems) and a power supply 18 (which furnishes the energy needs of the processor 8 and interface 9 subsystems). The interface input/output block 24 communicates with the controller input/output block 31 over an 8-bit bus ADAT<7:0>, which is multiplexed to communicate address and data information, and three control signals rdy, stb and dir to demultiplex and latch the address signals and provide direction control for data transmission. The controller input/output block 31 provides data and address lines ADAT<7:0> to the interface input/output block 24 and governs the operation of interface control signal lines, including data direction dir, ready rdy and strobe stb signal lines.

The interface input/output block 24 provides wakeup control signals on the bus ADAT<7:0> to the controller input/output block 31 to activate wakeup processing within the controller 28. The interface input/output block 24 controls wakeup lines, which are internal to the interface subsystem 9 and are separate from the wakeup lines within the processor subsystem 8.

The interface input/output block 24 includes memory-mapped registers (not shown) for processing wakeups. These registers are accessed by the controller 28 via the data bus ADAT<7:0>. The interface input/output block 24 generates wakeup signals arising from various circuits within the interface subsystem 9. These registers allow the controller 28 to control wakeups generated by the interface subsystem 9 in a manner similar to that which the controller 28 uses to control processor subsystem 9 wakeups. The controller 28 regulates the operation of the interface wakeups using read and write operations to the interface wakeup registers over the bus ADAT<7:0>. The controller 28 may read an interface wakeup flag register 168 of FIG. 3 to determine whether a particular interface wakeup has occurred and write to this register to force a wakeup to occur without regard to the state of the operations which normally activate such a wakeup. The controller 28 may write to an interface wakeup flag reset register (not shown) to clear an interface wakeup flag (not shown). The controller 28 may write to an interface wakeup mask register (not shown) to prevent interface operations which might activate a wakeup. An interface priority encoder circuit (not shown) within the interface input/output block 24, responds to an interface wakeup signal IWakeup by identifying the signal causing the interface wakeup and encoding this identity for reading by the controller 28 over the bus ADAT<7:0>.

Interface controller 15, upon receiving commands from the controller 28 via the interface input/output block 24, generates timed sequences of latched control signals to control the operations of the data acquisition circuit 20, the pace/sense analog circuit 16 and the power supply 18. The interface controller 15 starts each sequence, as designated and initiated by the controller 28, and provides a wakeup signal to the controller 28 when the sequence is finished.

The interface controller 15 communicates to other circuits within the interface subsystem 9 via subsystem-wide data, address and control buses IData, IAddr and ICtrl, respectively. Timing signals are provided for the interface subsystem 9 on 16 kHz and 131 kHz clock lines (not shown). The interface controller 15 sets latched control signals for interface subsystem circuits. The state of all control signals at one time, in combination with control information for the interface controller 15 itself, is called an "image".

Figure 3:
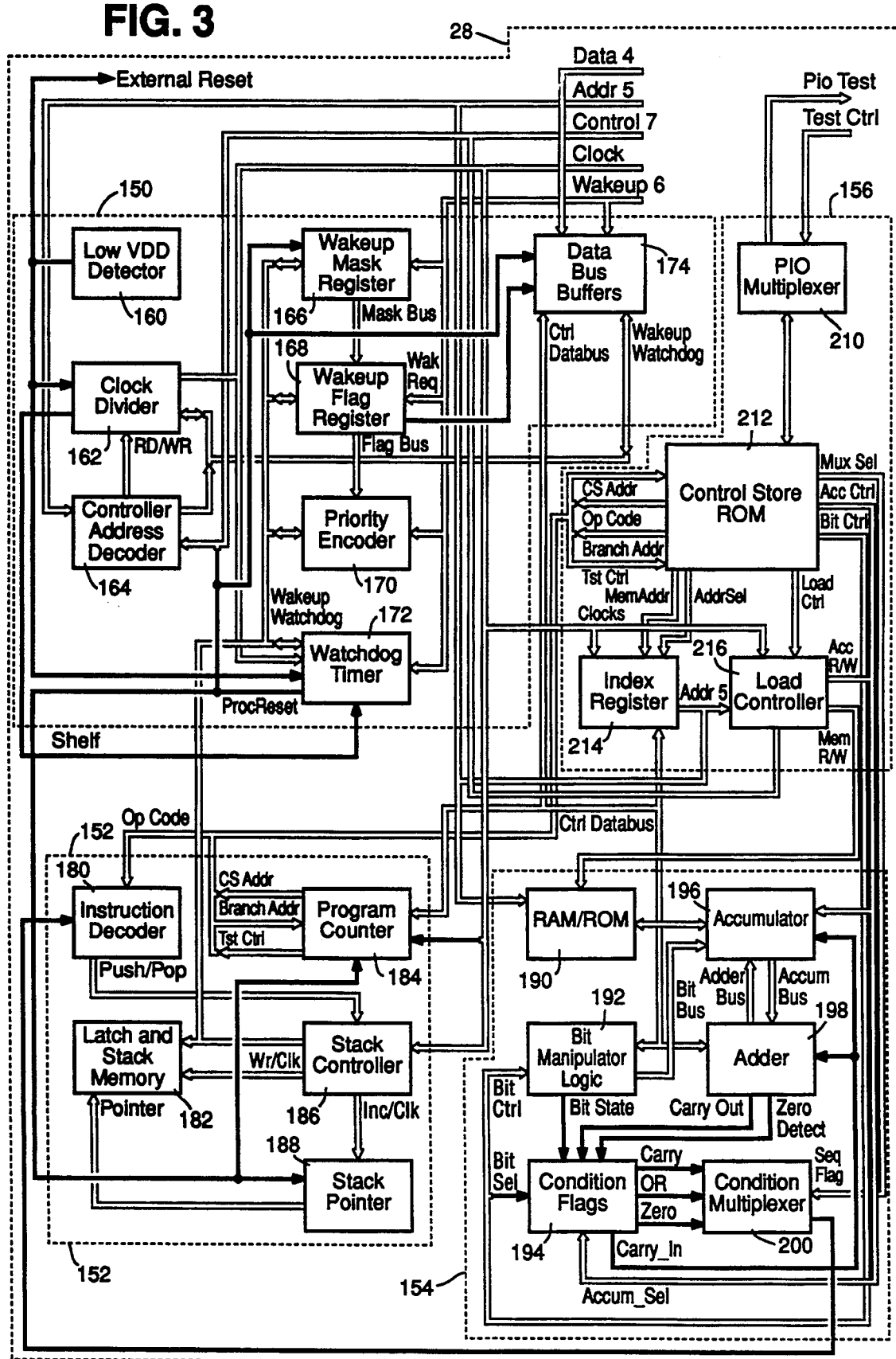
FIG. 3 is a high-level block diagram which illustrates the functional block elements of a controller shown in FIG. 2.

FIG. 3 illustrates a high-level block diagram of the controller 28. The controller 28 also includes circuits which perform administrative control operations. The controller 28 includes a watchdog timer 172 to restart the firmware program if a random access memory (RAM) mismatch error occurs or if a pacing cycle extends longer than 3 seconds. The watchdog timer 172 acts as a low rate timer which activates an error mode of operation to provide backup pacing when the stimulator 110 fails to conclude a cardiac cycle by the occurrence of the first of two possible events, pacing of the heart or sensing of a natural cardiac depolarization, within a predetermined time interval, here 3 seconds. Furthermore, the controller 28 exerts a system reset signal, through the operations of a low VDD detector 160, if the system power supply voltage falls below a value at which memories may not be retained. The low VDD detector 160 and the watchdog timer 172 are error detection circuits for detecting error conditions within the stimulator 110.

The controller 28 includes four parts: a test and wakeup block 150, a control sequencer 152, a memory and registers block 154 and a program controller 156. Input signals to the controller are a system reset signal external reset, a 32 kHz clock, four wakeup lines from external subsystems and various execution clock signals. Output signals which are provided by the controller 28 to exterior subsystems are a system-wide reset signal ProcReset, various clock subharmonic signals Clock, and digital data 4, address 5, and control 7 bus signals.

The test and wakeup block 150 includes data bus buffers 174 for communicating between the controller 28 and the timers 27, telemetry block 26, fast clock 29, and the controller input/output block 31. The test and wakeup block 150 processes wakeup signals arising outside or within the controller 28, using a wakeup mask register 166, a wakeup flag register 168 and a priority encoder 170. The control sequencer 152, in carrying out instructions contained in program controller 156, writes data to input/output mapped registers, including wakeup mask register 166, and wakeup flag register 168, which set up the wakeup operations governed by the operations of the test and wakeup block 150. The controller 28 can read the wakeup flag register 168 to determine whether a particular wakeup has occurred. The controller 28 can write to the wakeup flag register 168 to clear a wakeup flag or to force a wakeup to occur, regardless of whether the events which normally elicit a wakeup signal have occurred. The controller 28 may write to the wakeup mask register 166 to prevent operations which might otherwise activate a wakeup signal. The priority encoder register 170 responds to a wakeup signal by identifying the signal causing the wakeup and encoding this identity for reading by the controller 28. Whenever any wakeup flag is set, arising from inside or outside of the controller 28, the test and wakeup block 150 asserts a clock request signal on the clock bus, extending to the fast clock 29. In response to the clock request signal, the fast clock 29 supplies timing signals on the clock bus which drive the entire implantable device, but only when at least one wakeup request is active.

In addition, the test and wakeup block 150 includes a clock divider 162 providing clock division and generation functions as it divides a 32 kHz system clock signal, which is supplied to the controller 28 by the fast clock 29, into subharmonic frequencies of 16 kHz, 8 kHz, 4 kHz, 2 kHz and 1 kHz. The clock bus disseminates these subharmonic frequency signals to elements inside both the processor 8 and interface 9 subsystems. The clock divider 162 includes an input/output register which may be read or written by the controller 28. One of the signals in the clock divider 162 register, when set, disables the watchdog timer 172 by setting a shelf signal. When this signal is set, the processor subsystem 8 can remain in a dormant state without interruption from the watchdog timer 172. The shelf signal is used to initiate shelf mode operation, as is set forth hereinafter.

The test and wakeup block 150 also includes the aforementioned watchdog timer 172 and a low VDD detector 160. The watchdog timer 172 provides self-diagnostic testing capabilities for the controller 28. The watchdog timer 172 detects a condition in which the controller me fails to write a predefined key word to a key address at least once every 3 seconds. If this failure condition occurs, the watchdog timer 172 generates the processor subsystem 8 reset signal ProcReset, which starts the program memory in a control store read-only-memory (ROM) 212 of the program controller 156, at an address location 0 therein, by initializing a program counter 184 within the control sequencer 152. The watchdog timer 172 uses the 1 kHz clock signal on the clock bus for timing. The watchdog timer 172 is a counter which software can reset to zero by writing a key word to a key address. Software in a pacemaker application can read these keys from RAM and write them to the watchdog timer 172 register at the beginning of a pacing cycle. If the timer times out (for example, counts 3 seconds), it asserts the ProcReset signal for 1 ms, thus resetting all components of the processor subsystem 9 except the clock divider 162, which is required to time the 1 ms ProcReset signal. The watchdog timer 172 is comprised of a 12 bit ripple up counter clocked by the 1 kHz clock signal on the clock bus, which can only be reset by a system reset signal of the control 7 bus or by software writing a key word to the watchdog timer 172 register address.

The low VDD detector 160 provides another self-diagnostic capability, the testing of the supply voltage to ensure that sufficient power is available to maintain the safe functioning of volatile memory cells in data ram of the RAM/ROM block 190 within memory and registers block 154. The low VDD detector 160 circuit sets a system reset signal External Reset until the system voltage VDD rises to the level of two N-channel thresholds plus one P-channel threshold. The external reset signal causes a reset throughout the processor subsystem 8 via the ProcReset signal, and also calls for a reset in the interface subsystem 9 via outputs of the controller input/output block 31.

The program controller 156 contains program memory instructions and circuits for deriving control signals for executing the instructions. Each instruction of the control store ROM 212 includes an instruction field which specifies the conditional method for determining the next program counter 184 address. There are four conditional method codes, corresponding to CALL, BRANCH, JUMP and RETURN operations. In a CALL operation, the program counter 184 changes to an address designated by what is currently on the data bus data 4. In a BRANCH operation, the program counter 184 changes to an address designated by a branch address field in the instruction which sets the BranchAddr lines that extend to the program counter 184. In a JUMP operation, the program counter 184 changes to the designated branch address field of the instruction and the current value of the program counter 184 plus one is placed in a stack, as controlled by a stack controller 186. Later, when an instruction executes a RETURN operation, the program counter 184 takes the value in the stack.

The control store ROM 212 of program controller 156 provides the program memory which encodes all operations performed by the controller 28. Also within the program controller 156 are circuits for a load controller 216, and a hardwired index register 214. The index register 214 is a ten bit register which provides the addressing of data or input/output memory for controller instructions which employ indexed addressing.

The control store ROM 212 is made up of up to 4096 words. Each word is 38 bits long and includes a number of control fields. A four bit load control field selects the load controller 216 operation. A two bit data path field determines whether the data moving under the direction of the load controller 216 is altered en route by circuits within the memory and registers block 154, including bit manipulation logic 192, an adder 198 or a right shift operation of an accumulator 196.

The load controller 216 governs the data loading and storing operations of the controller 28, according to instructions encoded within each instruction of the program in the control store ROM 212 of program controller 156. Each instruction provides for data transmission between a particular source and destination.

The control sequencer 152 controls the order in which the controller 28 performs the sequence of program instructions contained within the control store ROM 212. The control sequencer 152 includes the program counter 184, an instruction decoder 180, the aforementioned stack and the stack controller 186, a stack pointer lee, and a latch and stack memory 182.

The stack pointer lee is a three bit register which points to the top of the latch and stack memory 182. The latch and stack memory 182 is eight registers of twelve bit words which address control store ROM 212 locations.

Memory and registers block 154 includes 512 bytes of data RAM and 512 data bytes of data ROM. Also within memory and registers block 154 are circuits and hardwired registers including the accumulator 196, the adder 198, bit manipulation logic 192, a RAM/ROM 190, condition flags 194, and a condition multiplexer circuit 200. The accumulator 196, adder 198 and bit manipulation logic 192 perform data manipulation, the result of which is communicated throughout the controller 28 via the eight bit data bus 4.

The accumulator 196 is an eight bit register which holds either loaded data or data resulting from add, subtract, rotate, and bit set or clear operations. The value of the accumulator 196 communicated throughout the controller as an accumulator bus accum bus signal.

Figure 4:
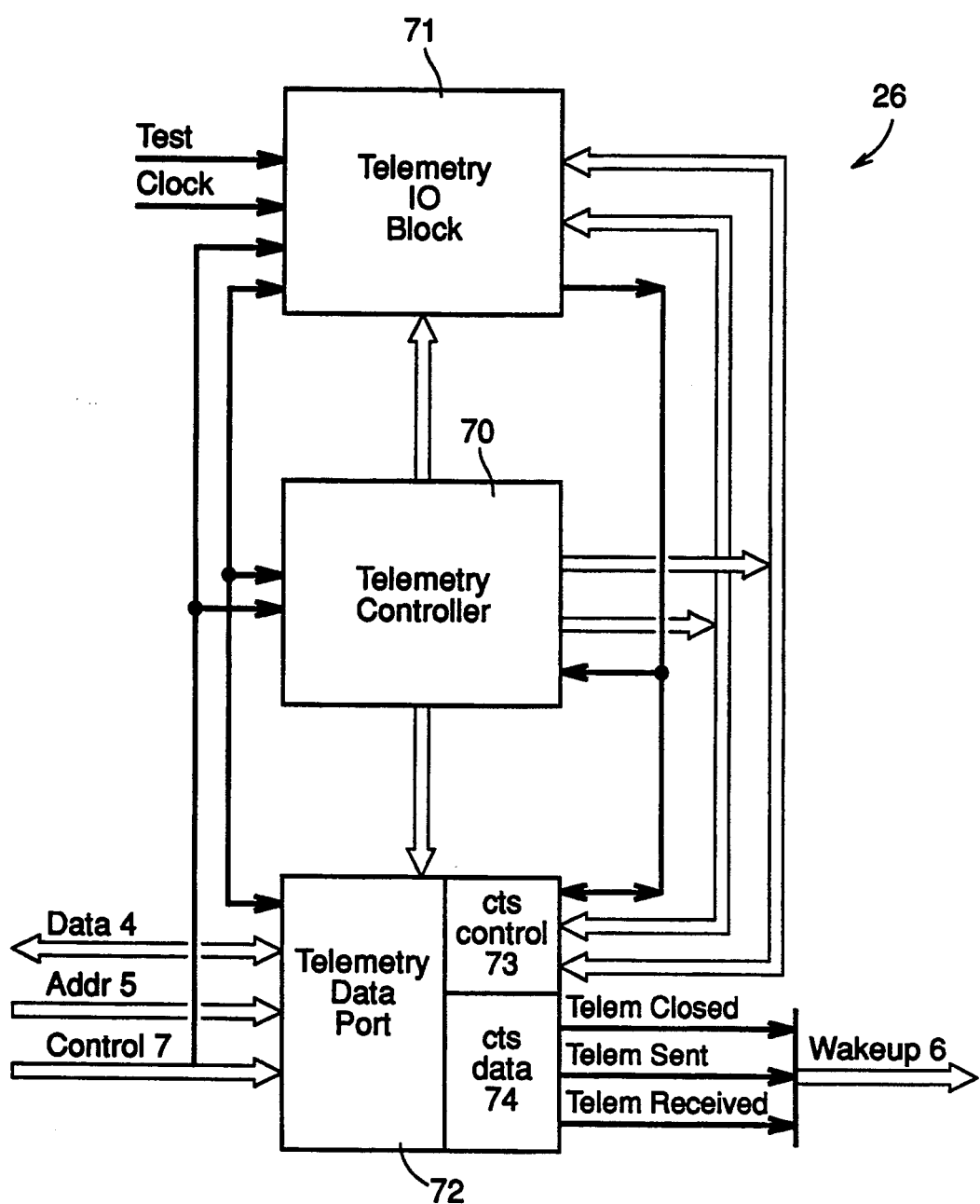
FIG. 4 is a high-level block diagram which illustrates the functional block elements of a telemetry block shown in FIG. 2.

FIG. 4 is a high level block diagram which illustrates the functional block elements of the telemetry block 26. Internally, the telemetry block 26 communicates with the controller 28 (FIG. 2) by means of two 8-bit memory-mapped interface registers, cts control 73 and cts data 74, and three wakeup request signals, CTS open, CTS sent and CTS received of Wakeup lines 6. When communication is active, the telemetry block 26 requires 32 kHz clock signals from fast clock 29 (FIG. 2), as discussed hereinafter, to provide internal timing events.

The telemetry block 26 comprises three subsystems: a telemetry controller 70, a telemetry input/output block 71 and a telemetry data port 72. The memory-mapped registers, cts control 73 and cts data 74, are components of the telemetry data port 72. The telemetry controller 70 is a control store firmware-based, control sequencer designed specifically for implantable applications. The telemetry input/output block 71 performs interfacing functions between the telemetry controller 70 and the controller 28. The telemetry input/output block 71 includes circuits which control the three wakeup request signals, CTS open, CTS sent and CTS received of Wakeup lines 6. The controller 28 governs the operations of the telemetry controller 70 by writing commands to memory-mapped wakeup control registers, wakeup flag reset, wakeup flag set and wakeup mask, within a controller input/output block (not shown but residing within the controller 28). Each of the wakeup flag reset, wakeup flag set and wakeup mask registers within this controller input/output block includes a control bit which corresponds to each of the CTS open, CTS sent and CTS received signals of Wakeup lines 6. The telemetry data port 72 includes a shift register for transmitting data to an external device one bit at a time, the aforementioned control status register cts control 73, and a transmit and receive buffer which, together, comprise the cts data register 74. The controller 28 reads and writes data to the external monitoring device computer system 100 (FIG. 1) by reading and writing data bytes to the cts data register 74.

A communication task is a routine performed by firmware within the stimulator 110 in response to a single command from the external monitoring device computer system 100. Each task is initiated when the computer system 100 sends a command word to the stimulator 110. Command word contents designate the type of communication to be performed (e.g., reading data from the system into the device, writing data from the device into the system, sending physiological data from the device to the system or requesting the device to perform an operation), the location within the stimulator 110 to read or write, and any required control information.

The power supply 18 (FIG. 2) is provided to transfer energy from a battery or cell 140 (FIG. 7) to four system supplies: a positive voltage supply VDD, a negative analog voltage supply A_NEG, an output pacing voltage supply O_TNK and a negative bias voltage supply V_NEG. These voltage supplies are defined as positive or negative with respect to a digital reference ground line VSS. VDD powers digital and analog systems in the stimulator 110. A_NEG powers some of the analog subsystems in the stimulator 110. O_TNK has a programmable amplitude, which is negative with respect to digital ground reference line VSS. V_NEG, the most negative voltage in the system, is used to bias P-wells and gates.

Figure 5:
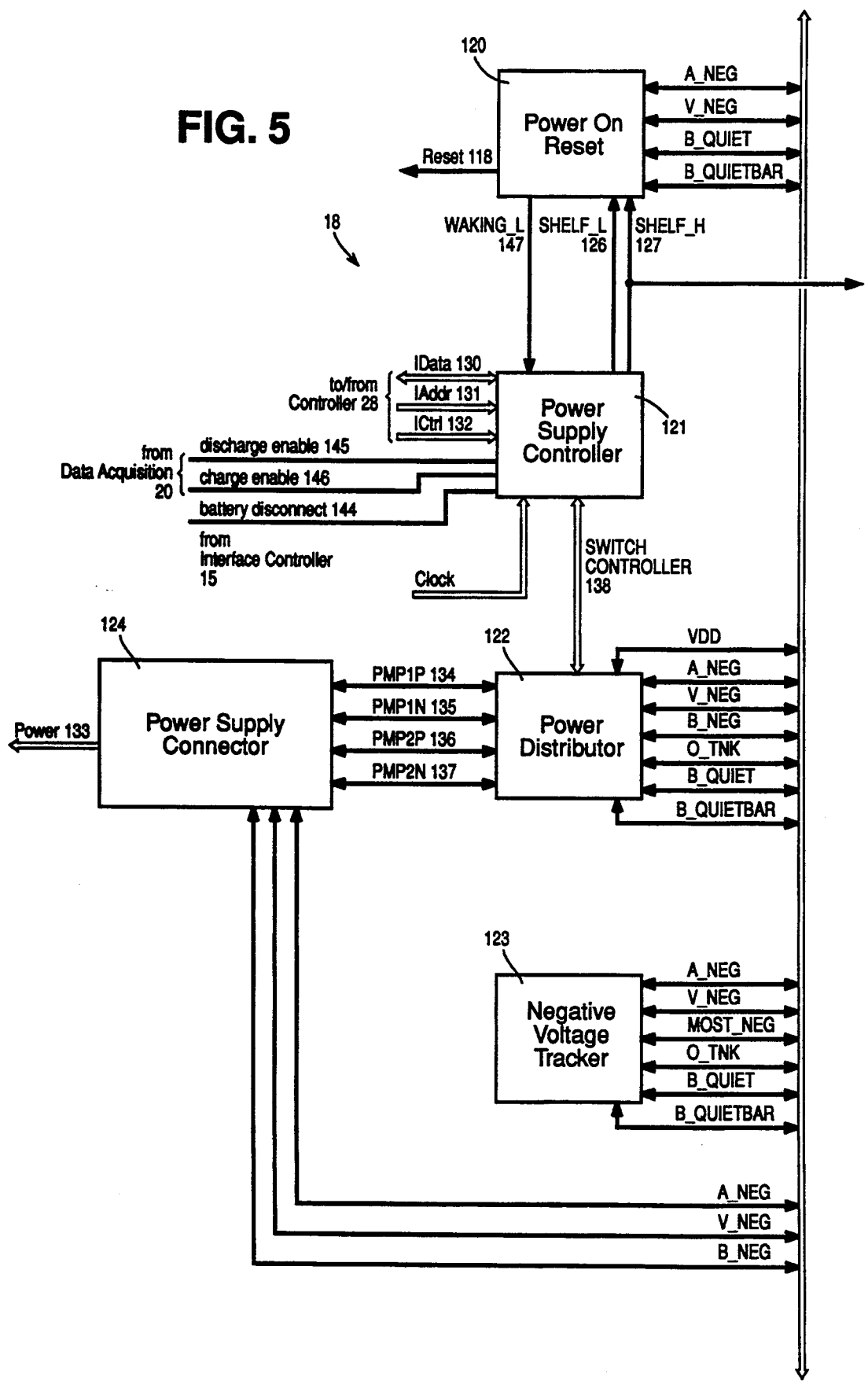
FIG. 5 is a high-level block diagram which illustrates the functional block elements of a power supply shown in FIG. 2.

FIG. 5 is a block diagram which depicts the circuit modules within the power supply 18, including a power on reset circuit 120, a power supply controller 121, a power distributor 122, a negative voltage tracker 123 and a power supply connector 124. The power on reset circuit 120 performs two main functions, driving circuits within the interface controller 9 to a stable and known state when power is applied, and detecting a low voltage error condition. The power supply controller 121, discussed hereinafter in more detail, receives input signals from the controller 28 and other circuits which determine how the power supply 18 will function. The power distributor 122, also discussed below in detail, distributes power to the four voltage supplies. The negative voltage tracker 123 maintains V_NEG close to the lowest potential on the interface subsystem 9 at all times, including power-up. The power supply connector 124 provides an interface between the power supply 18 and other circuits within the interface subsystem 9. It places voltage supplies and capacitor node voltages that are within the power supply 18, including A_NEG, V_NEG, PMP1P, PMP1N, PMP2P and PMP2N, upon a power bus 133 for this purpose.

Figure 6:
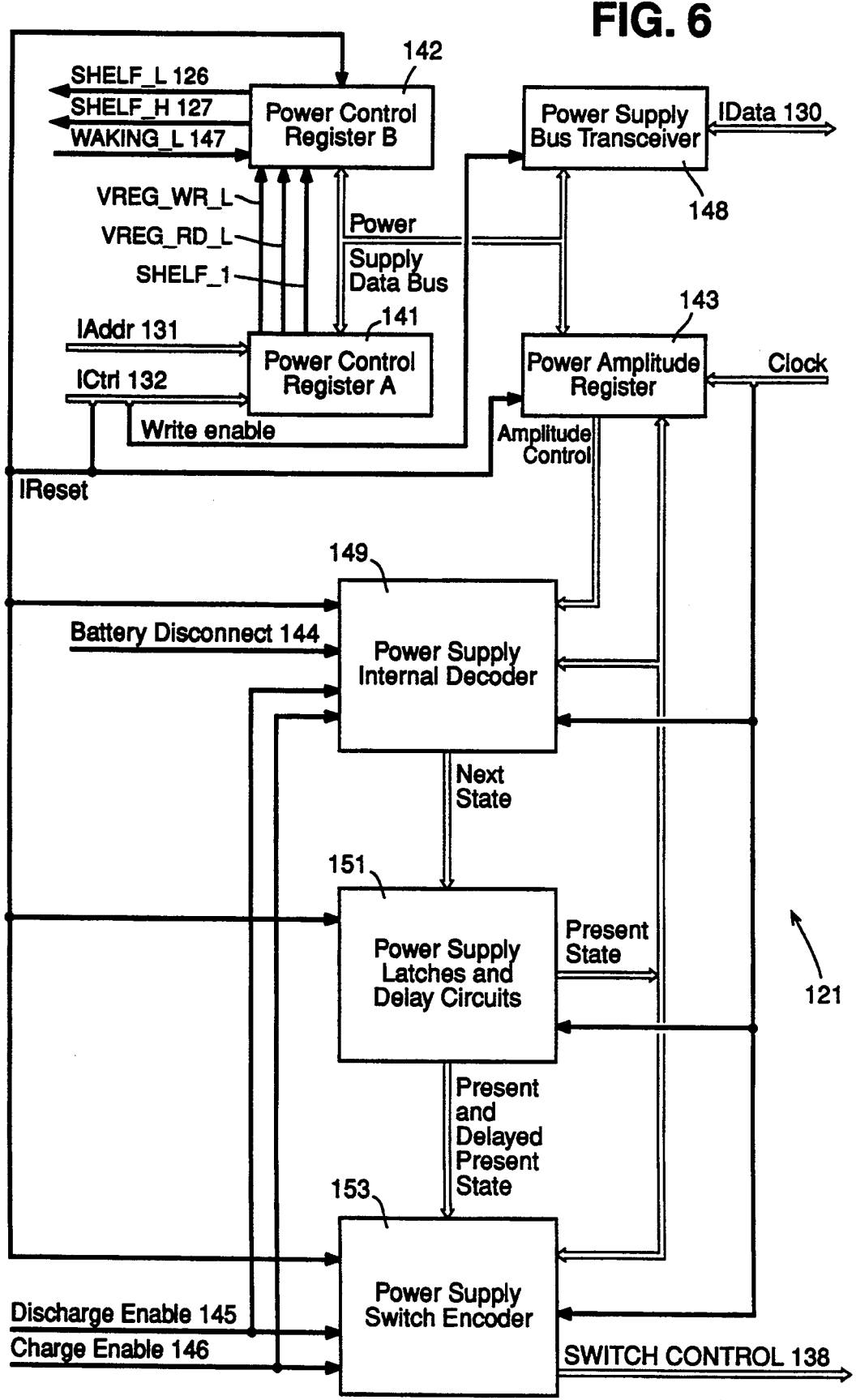
FIG. 6 is a high-level block diagram which illustrates the functional block elements of a power supply controller circuit shown in FIG. 5.

Referring to FIGS. 2 and 5-7, together, the power supply controller 121 receives input signals from the controller 28, the interface controller 15 and the data acquisition circuit 20. The power supply controller 121 provides gate voltage control signals for thirteen switches (S1-S12 of FIG. 7, discussed hereinafter), which connect the cell 140 to charge power supply capacitors (C2-C6 of FIG. 7) to their intended values. The circuit modules within the power supply controller 121 include three registers which the controller 28 can read and write to by means of address bus IAddr 131, control bus ICtrl 132 and data bus IData 130 (FIG. 6). These three registers are power control registers A 141 and B 142 and a power amplitude register 143. As is shown in FIG. 2, the communication between the controller 28 and the power supply 18 takes place indirectly, through the controller input/output block 31 and the interface input/output block 24. The intermediate blocks are necessary only if the controller 28 and power supply 18 circuits are located within physically different integrated circuit chips. In other embodiments of the invention, which require only a single circuit chip, the intermediate blocks are not necessary. The amplitudes of pulses generated by the stimulator 110 (FIG. 2) depend on the voltage of the cell 140 (FIG. 7) and a "charge pump factor", which designates a multiplier by which the cell voltage is multiplied to achieve an output pacing voltage supply O_TNK. The controller 28 writes codes which set the charge pump factor to the power amplitude register 143 (FIG. 6), a control register that provides the charge pump multiplication factor to a power supply internal decoder 149. The internal decoder 149 is a synchronous machine that changes state on an edge of a signal from the system clocks 19 to drive a power supply latches and delay circuits block 151, which determines and times the present state of the power supply 18. Signals from block 151 drive a power supply switch encoder 153, a circuit supplying the logic to drive the thirteen switches S1-S12 (FIG. 7) in the power distributor 122 by means of a SWITCH CONTROL signal.

The controller 28 writes codes to the power control registers A 141 and B 142 (FIG. 7) to set the time interval durations during which a tank capacitor C6 associated with the A_NEG supply and charge pump capacitors C2 and C3 for the O_TNK supply are charged, and to isolate the cell 140 from any supply.

Other inputs to the power supply controller 121 (FIG. 6) are a battery disconnect signal 144 from the interface controller 15 and, from the data acquisition circuit 20, a discharge enable signal 145 and a charge enable signal 146. The battery disconnect signal 144 commands the power supply 18 to connect the positive terminal of the cell 140 to VDD and leave its negative terminal open to enable cell resistance measurements. The discharge enable signal 145 and the charge enable signal 146 command the power supply 18 to charge or discharge the O_TNK voltage.

The power supply 18 generates various output signals. The power supply 18 generates a digital reset signal 118 (FIG. 5) if the system clocks 19 fail or if VDD falls to a point where logic may not operate if VDD falls further, but where memory retention is still guaranteed. The power supply 18 sets B_QUIET and B_QUIETBAR signals during system reset to minimize battery current so that RAM memories within the controller 28 can be retained during cold storage. The B_QUIET and B_QUIETBAR signals, when set, shut down all current sources in the interface subsystem 9 except the crystal oscillator current source for the system clocks 19. The B_QUIET signal can be set by means of a shelf mode signal from an external programmer, such as the external monitoring device 100 of FIG. 1. The shelf mode signal causes the power supply 18 to disable all circuits within the interface subsystem of FIG. 2, other than the system clocks 19.

The power supply 18 distributes the energy of the cell 140 using the power distributor 122 of FIG. 5. The power distributor 122 periodically charges capacitors on VDD (tank capacitor C4 of FIG. 7), A_NEG (tank capacitor C6), and O_TNK (tank capacitor C5 and charge pump capacitors C2 and C3). V_NEG follows the amplitude of the most negative voltage, according to the operations of the negative voltage tracker 123 (FIG. 5). The controller 28, acting via signals through the interface controller 15, can disable the power distributor 122 by setting the battery disconnect line 144 so that another chip can use the cell.

Figure 7:
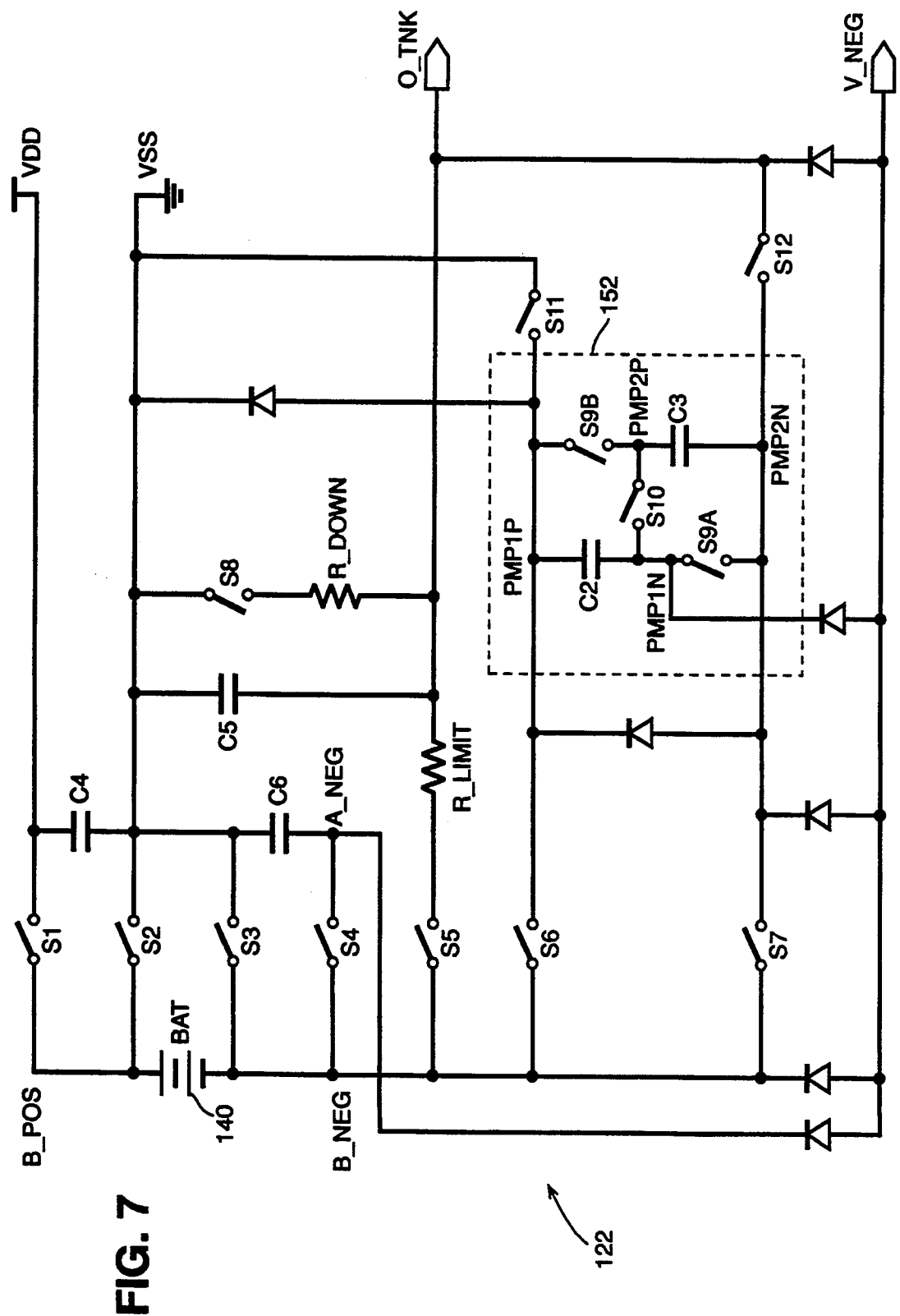
FIG. 7 is a circuit diagram which illustrates the functional circuit elements of a power distributor circuit shown in FIG. 5.

Referring to FIG. 7, the circuit of the power distributor 122 illustrates that VDD, O_TNK and A_NEG tank capacitors C4, C5 and C6, respectively, are charged directly from the cell 140 but the O_TNK charge pump capacitors C2 and C3 are charged via one of four pumping modes, depending on the programmed charge pump factor. The fraction of time the cell spends charging a tank capacitor is called the dwell.

The data acquisition circuit 20 (FIG. 2) supplies the discharge enable 145 (FIG. 5) and charge enable 146 signals to provide most of the control of the O_TNK voltage. However, the power supply 18 determines the timing of O_TNK discharging and charging by independently providing dwell timing.

The circuit diagram of FIG. 7 depicts the components of the power distributor 122. The cell 140, which is preferably a lithium battery cell known in the art of cardiac pacemakers, is connected between VSS and one of the voltage supplies A_NEG, V_NEG, O_TNK or VDD, using various settings of thirteen switches S1, S2, S3, S4, S5, S6, S7, S8, S9A, S9B, S10, S11 and S12. Switches S1 and S2 are connected to a positive battery terminal B_POS of the cell 140. Switches S3, S4, S5, S6 and S7 are connected to a negative battery terminal B_NEG of the cell 140.

To charge the VDD tank capacitor C4 directly from the cell 140, the power supply 18 places switches S1 and S3 in a closed state and establishes an open state for the remaining 11 of the thirteen switches. The power supply also charges the A_NEG tank capacitor C6 directly from the cell 140 by closing switches S2 and S4 while the other switches are open.

The power supply 18 charges an O_TNK supply capacitor C5 from the cell 140 according to one of four programmable pumping modes, which depend on the programmed charge pump factor. The settings of switches S5, S7, S9A, S9B, S10 and S11 depend on the pumping mode.

A charge pump 152 consists of two charge pump capacitors C2 and C3 and switches S9A, S9B and S10. There are four charge pump capacitor nodes, PMP1P, PMP1N, PMP2P and PMP2N, which are connected via respective lines 134, 135, 136 and 137 to the power supply connector 124 of FIG. 5. The pump capacitors C2 and C3 are in series when switch S10 is closed while switches S9A and S9B are open; they are in parallel when either of switches S9A or S9B is closed while switch S10 is open; and, they are respectively shorted when switch S10 and a corresponding one of either of switches S9A and S9B is closed. The charge pump 152 operates according to the programmable selection of the charge pump factor MX, which can be set to 1×, 1.5×, 2× or 3×. When the charge pump factor is 1×, the cell 140 charges the O_TNK supply capacitor C5 directly. When the charge pump factor is 1.5× or greater, the cell 140 charges the O_TNK supply capacitor C5 via the charge pump 152 circuit, which multiplies the charge using pump capacitors C2 and C3.

The charge pump 152 operates in two timing phases, a charge phase and a discharge phase. During the charge phase, the charge pump 152 charges the two pump capacitors C2 and C3 from the cell 140. During the discharge phase, the charge pump 152 discharges the cell 140 and the two pump capacitors C2 and C3 into the O_TNK supply capacitor C5. The switches shown in FIG. 7 are set or reset in a manner which depends on the charge pump factor and the current timing phase in which the charge pump 152 is operating. During the charge and discharge phases, the switches are set in the manner discussed hereinafter.

When the pump capacitors C2 and C3 and the cell 140 have been discharged into the O_TNK supply capacitor C5, the voltage on C5 may be applied to the lead 11 of FIG. 1 to generate a pacing pulse to the heart 1, discharging the O_TNK capacitor C5, by the operation of the interface controller 15 and the pace/sense analog circuit 16 of FIG. 2. In the event that the desired pacing pulse amplitude is changed by the controller 28 before the O_TNK capacitor C5 has been discharged by means of the delivery of a pacing pulse, the controller 28 may cause the discharge of C5 by issuing a command which causes the switch S8 to close and all other switches to open, thereby discharging the O_TNK capacitor C5 into the bleed down resistor R_DOWN.

When the charge pump factor is 1×, switches S2, S5, S9A, S9B and S10 are closed while the remaining eight switches are open, during the charge phase of the charge pump 152 cycle. Current flows from the B_POS terminal of cell 140 through switch S2, the O_TNK supply tank capacitor C5, resistor R_LIMIT and switch S5 to the cell's B_NEG terminal during the charge phase, charging capacitor C5 to the level of cell 140. The tank capacitor C5 is associated with the O_TNK supply and, when the charge pump factor is 1×, provides a tank voltage equal to the cell 140 potential. Switches S9A, S9B and S10 are closed under these conditions so that the pump capacitors C2 and C3 are shorted and no current flows from PMP1P to PMP2N.

When the charge pump factor is greater than 1×, the tank capacitor C5 provides a voltage which is a multiple of the cell 140 voltage. Thus, when the charge pump factor is 1.5× during the charge pump 152 charge phase, switches S2, S7, S10 and S11 are closed, while the remaining nine switches are open. Current flows from the B_POS terminal of cell 140 through switch S2, switch S11, pump capacitor C2, switch S10, pump capacitor C3 and switch S7 to the cell's B_NEG terminal. Thus, the pump capacitors C2 and C3 are connected in series and current flows from PMP1P through PMP1N and PMP2P to PMP2N, charging each of the capacitors C2 and C3 to one-half of the voltage of cell 140. During the discharge phase, switches S2, S6, S9A, S9B and S12 are closed while the remaining eight switches are open, so that the two pump capacitors C2 and C3 are mutually placed in parallel and placed in series with the cell 140. Thus, the cell 140 and pump capacitors C2 and C3 are discharged into the O_TNK supply capacitor C5. In this manner, during the discharge phase the pump capacitors C2 and C3 in parallel, having been charged to one-half of the cell voltage, in series combination with the cell 140, are discharged into the O_TNK supply capacitor C5, charging that capacitor to 1.5 times the cell voltage. During the next charge phase, the cell 140 recharges the pump capacitors C2 and C3 in series, again each to one-half of the cell voltage, to prepare them for the next discharge phase. Overall, the O_TNK supply capacitor C5 is charged to 1.5 times the cell 140 voltage.

When the charge pump factor is 2× during the charge pump 152 charge phase, switches S2, S7, S9A, S9B and S11 are closed, while the remaining eight switches are open. Current flows from the B_POS terminal of cell 140 through switch S2, switch S11, pump capacitor C2 and pump capacitor C3 in parallel via switches S9A and S9B, respectively, and switch S7 to the cell's B_NEG terminal. Thus, the pump capacitors C2 and C3 are connected in parallel in the circuit and current flows from PMP1P through PMP1N and from PMP2P through PMP2N, charging each of the capacitors C2 and C3 to the full value of the voltage of cell 140. During the discharge phase, switches S2, S6, S9A, S9B and S12 are closed while the remaining eight switches are open, so that the two pump capacitors C2 and C3 remain connected in parallel and are placed in series with the cell 140 and O_TNK supply capacitor C5. Thus, the cell 140 and pump capacitors C2 and C3 are discharged into the O_TNK supply capacitor C5. In this manner, during the discharge phase the pump capacitors C2 and C3 in parallel, having been charged to the cell voltage, in series combination with the cell 140, are discharged into the O_TNK supply capacitor C5. During the next charge phase, the cell 140 recharges the pump capacitors C2 and C3, each to the full value of the cell voltage, to prepare them for the next discharge phase. In all, the O_TNK supply capacitor C5 is charged to 2 times the cell 140 voltage.

When the charge pump factor is 3× during the charge pump 152 charge phase, switches S2, S7, S9A, S9B and S11 are closed, while the remaining eight switches are open. Current flows from the B_POS terminal of cell 140 through switch S2, switch S11, through parallel paths through pump capacitors C2 and C3, and through switch S7 to the cell's B_NEG terminal. The flow in the parallel circuit is from switch S11 through pump capacitor C2 and switch S9A to switch S7 in one path, and from switch S11 through switch S9B and pump capacitor C3 to switch S7 in a second path. Thus, the pump capacitors C2 and C3 are connected in parallel and each is charged to the full value of the voltage of cell 140. During the discharge phase, switches S2, S6, S10 and S12 are closed, while the remaining nine switches are opened, so that the two pump capacitors C2 and C3 and the cell 140 are all placed in series with, and discharged into, the O_TNK supply capacitor C5. In this manner, during the discharge phase the pump capacitors C2 and C3 in series, each having been charged to the full cell voltage, and the cell 140 are all connected in series with, and are discharged into, the O_TNK supply capacitor C5. During the next charge phase, the cell 140 again recharges the pump capacitors C2 and C3, each to the full value of the cell voltage, to prepare them for the next discharge phase. In all, the O_TNK supply capacitor C5 is charged to 3 times the cell 140 voltage.

Figure 8:
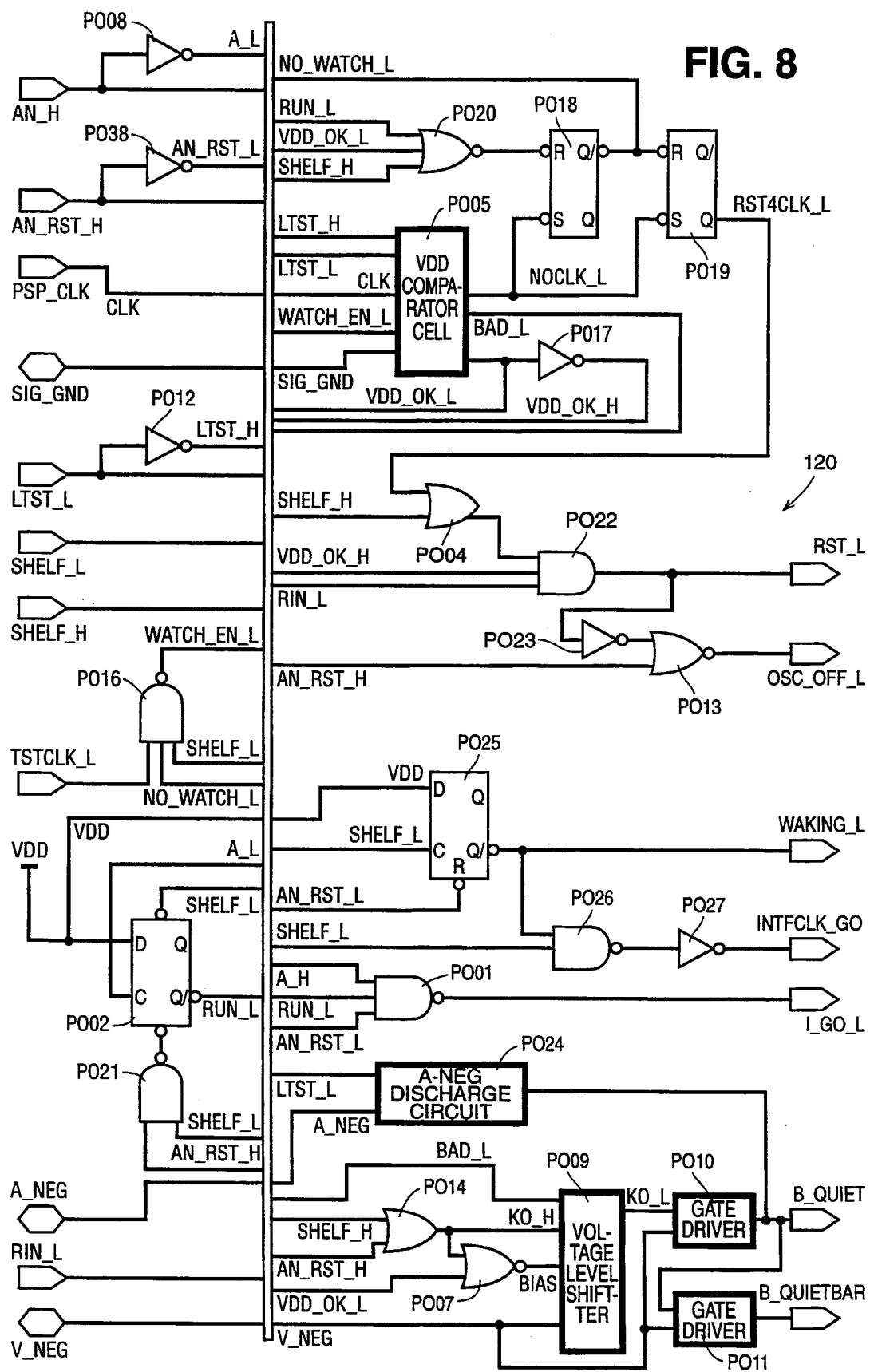
FIG. 8 is a circuit diagram which illustrates the functional circuit elements of a power on reset circuit shown in FIG. 5.

In addition to the switches and components shown in FIG. 7, the power distributor 122 includes circuits (not shown) which drive, correctly bias and provide level shifting for the switches S1-S12. Referring to FIG. 8 in conjunction with FIGS. 2, 5, 6, and 7, the power on reset circuit 120 drives circuits within the interface controller 9 to a stable and known state when power is applied and detects a low voltage error condition. The power on reset circuit 120 operates as an asynchronous state machine in one of five stable states, including RUN, VDD reset, clock reset, clock start and I_BIAS start states, which are discussed in greater detail hereinafter. (Intermediate unstable states may occur when one stable state is progressing to the next, but such unstable states do not affect the performance of the circuit.) The RUN state is the normal operating state of the stimulator 110 and occurs when a B_QUIET signal, a B_QUIETBAR signal, a reset signal RST_L, an oscillator off signal OSC_OFF_L, and an I go low signal L_GO_L all have a digital level of 0 (i.e., they are "not set"). The RST_L signal, when set (i.e., to a digital level of 1), requests the processor subsystem 8 to call for a system-wide reset. The OSC_OFF_L signal is set when the interface subsystem 9 is reset. When set, the OSC_OFF_L signal disables the crystal oscillator current source of system clocks 19. The L_GO_L signal is an output from the power on reset circuit 120 which, when set, instructs a bias generator (not shown) in the data acquisition circuit 20 of FIG. 2 to startup the main current sources of the interface subsystem 9.

In the RUN state, the cardiac stimulator 110 operates in a "normal" state, in which the stimulator 110 performs standard procedures such as generating stimulus pulses and sensing physiological signals. The RUN state endures until a catastrophic failure occurs, such as failure of the system clocks 19 or failure of the power supply 18 (VDD failure). In addition, an external programmer may write a command to the stimulator 110 to cause the stimulator 110 to enter a shelf mode of operation in which the power on reset circuit 120 no longer operates in the RUN state.

The power on reset circuit 120 includes a VDD comparator cell PO05, which has a VDD OK output signal VDD_OK_L. VDD_OK_L maintains a voltage level of VDD until VDD is greater than a VDD comparator threshold, at which point VDD_OK_L takes a value of VSS. The VDD comparator threshold value is the sum of the p channel threshold and the n channel threshold of the integrated circuit chip of the subsystem 9. The VDD comparator cell PO05 also monitors the operation of system clocks 19 and if there is no change in state of a CLK signal from system clocks 19 for a predetermined time, then the VDD comparator cell PO05 sets a reset request, called NOCLK_L. The NOCLK_L signal is also set when VDD fails to be greater than the VDD comparator threshold value.

When the VDD comparator cell PO05 detects a VDD failure, the power on reset circuit 120 enters a VDD reset state. When the VDD comparator cell PO05 detects a VDD failure, the VDD_OK_L signal is reset, causing an inverter PO17 to set a VDD_OK_H signal which, through the operation of AND gate PO22, sets a RST_L signal. The RST_L signal propagates through the interface subsystem 9 to cause a system reset. Through the operation of other circuits, discussed hereinafter, the B_QUIET signal, the B_QUIETBAR signal and the OSC_OFF_L signal are also set. These set-tings of the B_QUIET, B_QUIETBAR and OSC_OFF_L signals greatly reduce cell current and set switches (to be discussed hereinafter with respect to shelf mode operation) operating on the power supply controller 121 and the power distributor 122 which guarantee that the lithium cell 140 is connected to charge VDD, even if circuit logic is no longer operable due to a low VDD voltage level. When VDD is again adequate for logic to function, the VDD_OK_H signal goes high and an AN_RST_H signal goes low logic, and the power on reset circuit 120 terminates the VDD reset state and enters a clock start state. The AN_RST_H signal is an input to the power on reset circuit 120 which is set by the interface input/output circuit 24 when the processor subsystem 8 sets read, write, and address strobe signals calling for a system reset. The AN_RST_H signal causes the interface subsystem 9 to set B_QUIET, B_QUIETBAR and OSC_OFF_L signals.

When the VDD comparator cell PO05 detects a clock CLK failure, it pulls the system reset line RST_L to VSS (via resetting (to digital 0) of the VDD_OK_L signal, leading to setting (to digital 1) of the VDD_OK_H signal) and causes the power on reset circuit 120 to enter a clock reset state, which is similar to the VDD reset state. The system reset signal RST_L remains set for 0.2 to 2 mS, a sufficient duration to set the RST_L line to the VSS voltage, as the circuit in the VDD comparator cell PO05 acts in the manner of a "one-shot", in which the VDD comparator cell PO05 controls the NOCLK_L signal operating on an SR flip-flop PO19 to time a reset clock signal RST4CLK_L. The RST4CLK_L signal which, through the operation of an OR gate PO04 and AND gate PO22, sets the RST_L signal. When the RST_L signal level recovers, the VDD_OK_H signal goes high and an AN_RST_H signal goes low logic and the power on reset circuit 120 terminates the VDD reset state and enters a clock start state.

During the clock start state, the OSC_OFF_L signal provides a current to a crystal oscillator (not shown) which drives the timing of the stimulator 110. After the crystal oscillator starts, the power distributor 122 charges the VDD supply, then charges the A_NEG, and at that moment the power on reset circuit 120 terminates the Clock Start state and enters an I-BIAS Start state. In this state B_QUIET, B_QUIETBAR and OSC_OFF_L are reset (to 0, 1 and 1, respectively).

When the power distributor 122 charges the A_NEG supply, it sets an A_H signal. The A_H signal is an input to the power on reset circuit 120 which, when set, indicates that the power distributor 122 is charging the A_NEG supply. When the A_H signal occurs for the first time during the reset procedure, the power on reset circuit 120 sets an I_GO_L signal which designates that an I-BIAS state is in process. In this state, switch S1 (FIG. 7) on the VDD supply line keeps VDD high so it doesn't cause another reset (except perhaps at extreme sub-zero shipping temperatures). The power distributor 122 charges A_NEG. The power distributor 122 switches from charging A_NEG to charging O_TNK or VDD one cycle of 8 KHz after a 250 Hz INTF_250 timing signal (not shown) of a power supply clock bus PSP_CLK (not shown) goes low. At that moment, the I_GO_L signal is reset and the power supply circuit 18 enters the RUN state.

When the stimulator 110 is shipped from the factory, it may be shipped in a special low current mode, called shelf mode, in which much less energy is depleted from the cell 140 before implantation. In shelf mode, it is intended that the stimulator 110 will only have its telemetry function enabled. Other operations, such as the generation of stimulating pulses, the sensing of electrical signals, and the performance of self-diagnostic tests and measurements, are disabled. In shelf mode, the power supply 18 supplies power to VDD alone. A_NEG, V_NEG and O_TNK supplies are disabled.

Figure 11:
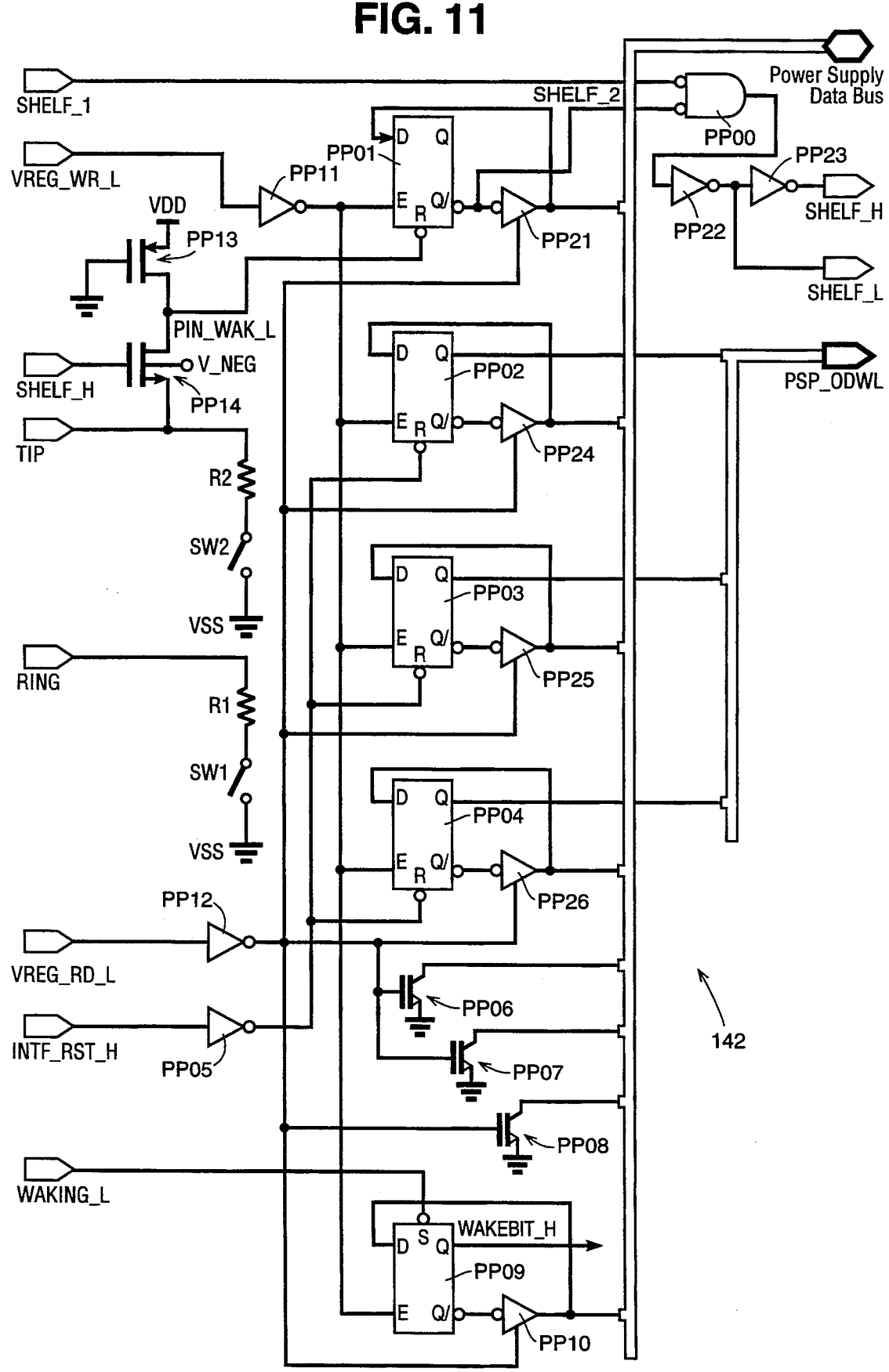
FIG. 11 is a circuit diagram which illustrates circuitry for a power control register B shown in FIG. 6.

The controller 28, upon receiving a command from the external programmer 100 of FIG. 1 via telemetry block 26, writes codes to power control registers A 141 and B 142 which cause the power supply 18 to place the interface subsystem 9 in a low power shelf mode. Referring to FIG. 5 and FIG. 6 in conjunction with the circuit diagram of FIG. 11, which illustrates the power control register B 142, the controller 28 sets one signal bit SHELF_1 in power control register A 141 and one signal bit SHELF_2 in power control register B 142, causing circuitry in the power control register B 142 to control the two shelf mode bits SHELF_H and SHELF_L. Referring to FIG. 11, signals from the controller 28 to the power control register B 142 set the digital value of signals on a Power Supply Data Bus. One of these signals is input to a delay (D) flip-flop PP01 within the power supply control register B 142 to set the SHELF_2 signal bit. Signals from the controller 28 via the Power Supply Data Bus to the power control register A 141 set the digital value of the SHELF_1 signal bit, which is input to the power control register A 142 by means of a connection to NOR gate PP00. When the controller 28 sets both register signal bits SHELF_1 and SHELF_2, the interface subsystem 9 enters shelf mode when the power control register B 142 sets SHELF_H and SHELF_L. SHELF_H and SHELF_L are then input at 127 and 126, respectively, to the power on reset circuit 120 from the power supply controller 121. The SHELF_H signal input 127 to the power on reset circuit 120 is used to enter a low current mode which sets B_QUIET and B_QUIETBAR. The low current mode allow the systems clocks 19 to run, which is required for telemetry 26 on the processor subsystem 8 to work.

Figure 9A:
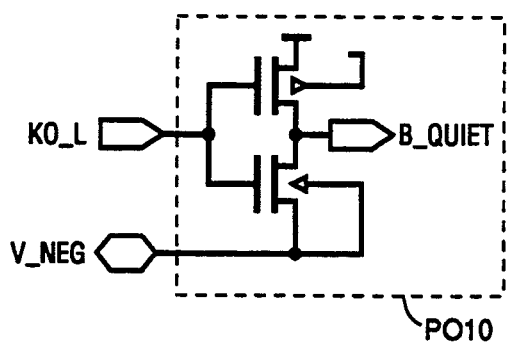
FIGS. 9A, 9B, 9C and 9D are circuit diagrams showing detailed depictions of four circuit blocks within the power on reset circuit shown in FIG. 8.
Figure 9B:
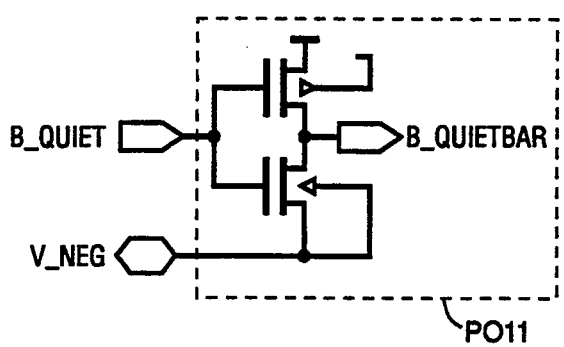
Figure 9C:
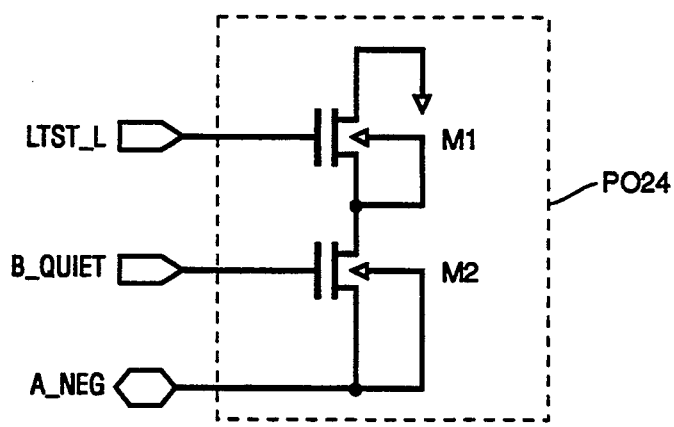
Figure 9D:
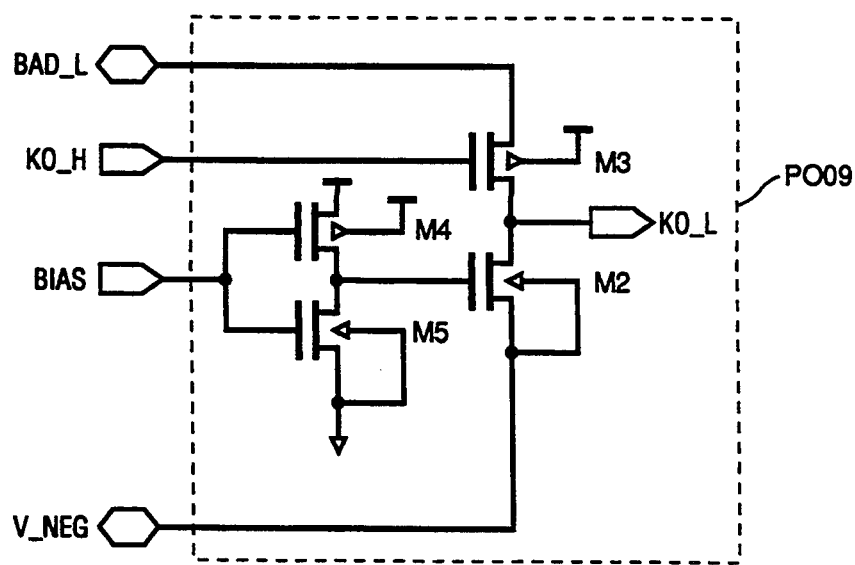
Figure 10:
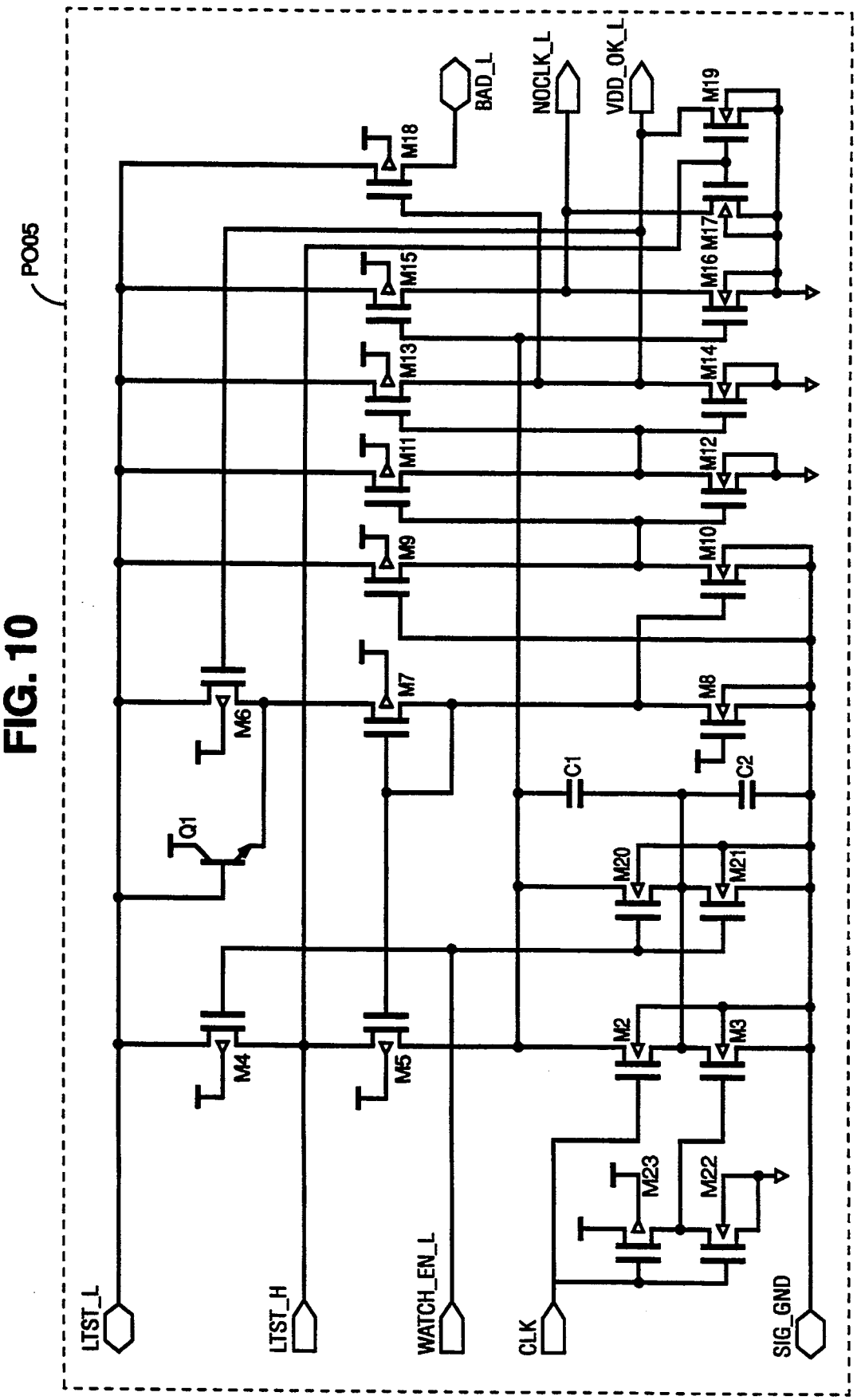
FIG. 10 is a circuit diagram showing a detailed depiction of a fourth circuit block within the power on reset circuit shown in FIG. 8.

Referring to FIG. 8, FIG. 9A, FIG. 9B, FIG. 9C, FIG. 9D and FIG. 10, the and interface subsystem 9 integrated circuit (IC) chips before their assembly into a stimulator 111 in order to put the chips into a leakage current configuration. When asserted, these signals power off all circuitry on the interface IC chips and reduce the current consumption to p-n junction leakage levels only. This procedure is used during preliminary IC chip tests to quickly evaluate if there are gross leakage problems or erroneous shorts in the IC chips. Any IC chips that fail this first test are discarded as failures, saving IC chip test time in production. The LTST_L and LTST_H signals are always de-asserted (i.e., LTST_L=VDD and LTST_H=VSS) when the IC chips are assembled into the stimulator, and they enable normal operation in this mode. The SHELF_H signal causes B_QUIET and B_QUIETBAR to be set via a voltage level shifter circuit PO09 (FIGS. 8 and 9C) and gate drivers PO10 and PO11 (FIGS. 8 and 9A). The B_QUIET and B_QUIETBAR signals disable all of the analog bias sources of the interface subsystem 9 and place all digital outputs in a defined state. The B_QUIET signal causes an A_NEG discharge circuit PO24 to discharge the A_NEG capacitor C6 (FIG. 7) to ground level (VSS). During the low current mode when B_QUIET is asserted, the shorting of the A_NEG capacitor C6 will further reduce battery current by disabling analog functions that utilize the A_NEG supply. The power supply 122 (FIG. 7) will cease to charge the A_NEG capacitor C6 until the B_QUIET signal is de-asserted. The level shifter circuit PO09 is required to set the voltage level of the B_QUIET and B_QUIETBAR to VDD and V_NEG, rather than the standard interface subsystem 9 levels of VDD and VSS.

The SHELF_L signal disables a NAND gate PO21 (FIG. 8) to block the analog reset signal AN_RST_H from resetting a D flip-flop PO02. This is necessary for a wake up sequence for recovering from shelf mode, which is discussed hereinafter. The SHELF_L signal also disables a NAND gate PO26, thereby causing an INTFCLK_GO signal to go low. The INTFCLK_GO signal is one of the signals on the Clock bus shown in FIG. 2 and, when it is asserted, it disables the clock divider 16 of FIG. 3 in the processor subsystem 8. The clock divider 162 continues to operate normally, providing clock signals to the processor subsystem 8 while the interface subsystem 9 clock signals are disabled. The SHELF_L signal also sets the D flip-flop PO02, thereby setting a RUN_L signal to enable a three input NOR gate PO20 so that the power on reset 120 will operate correctly when a wakeup sequence is initiated. The SHELF_H signal disables a 3 input NAND gate PO16 and sets its output, a clock watcher enable signal WATCH_EN_L, high to disable a clock watcher function in the VDD comparator cell PO05 so that the absence of a change of state of the interface clock CLK at the VDD comparator cell PO05 input does not cause a system reset. The clock watcher output NOCLK_L stays high. The SHELF_H signal disables the OR gate PO04 so that the reset clock signal RST4CLK_L is disabled during shelf mode. RST4CLK_L must be disabled because the outputs of a set/reset (SR) flip-flop PO19 are undefined during shelf mode at power up because both of its inputs are held high. The SHELF_H signal also disables the 3 input NOR gate PO20, which holds a SR flip-flop PO18 in its reset state to hold a NO_WATCH_L signal high. This enables the 3 input NAND gate PO16 so that the power on reset 120 will operate correctly when a wakeup sequence is initiated.

At this point, the interface subsystem 9 is in shelf mode, waiting for the resetting of the shelf mode signals SHELF_1 or SHELF_2 via a handheld programmer.

When an external programmer, such as the external monitoring device 100 of FIG. 1, resets either the SHELF_1 signal bit in power control register A 141 or the SHELF_2 bit in power control register B 142, the NOR gate PP00 and inverters PP22 and PP23 in the power control register B 142 (see FIG. 11) immediately reset the two shelf mode bits SHELF_H and SHELF_L and the following wakeup sequence occurs. Referring again to FIG. 8, resetting of the SHELF_H signal causes B_QUIET and B_QUIETBAR to be reset by the operation of the voltage level shifter circuit PO09 (FIG. 9D) and gate drivers PO10 (FIG. 9A) and PO11 (FIG. 9B), causing all of the analog bias sources in the interface subsystem 9 to be enabled as soon as the I_GO_L signal is set. The setting of I_GO_L was discussed previously in connection with the operation of the I_BIAS state. Accordingly, the SHELF_L signal goes high, enabling the NAND gate PO21 (FIG. 8). Thus, when the analog reset signal AN_RST_H occurs, which follows immediately, the D flip-flop PO02 will be reset. As the SHELF_L signal goes high, it enables the NAND gate PO26. However, since the programming operation takes place when the cardiac stimulation device 110 is functioning normally and VDD is supplying its power, the VDD input to the flip-flop P025 is set. The SHELF_L signal is the clock input of the D flip-flop PO25 and, as the SHELF_L signal goes high, the Q/ output of PO25 goes low because the VDD input to P025 is set at this time, holding the INTFCLK_GO signal low and causing the clock divider 162 of FIG. 3 to remain disabled.

At this point, the power on reset circuit 120 will soon enable the clock watcher function in the VDD comparator cell PO05 by setting the clock watcher enable signal WATCH_EN_L but at the present time it holds the clock watcher clock output NOCLK_L in a disabled state by holding the INTFCLK_GO signal low, thereby allowing the VDD comparator cell PO05 clock watcher function to cause a system reset. The Q/ output signal of the D flip-flop PO25 also sets a WAKING_L signal, which sets a WAKEBIT_H bit in the power control register B 142 (FIG. 11), sending a wakeup signal to the processor subsystem 8 after a system reset is initiated.

The WAKEBIT_H may be read by the controller 28 for diagnostic purposes. If the stimulator 110 is in a reset condition and the WAKEBIT_H signal is set, the reset condition results from initiation of shelf mode. However, if the stimulator 110 is in a reset condition and the WAKEBIT_H signal is not set, the reset condition results from an error condition, in which case the controller 28 may activate a special "safety" operating mode for the stimulator 110.

There are further consequences which ensue when the SHELF_L signal goes high. Setting of the SHELF_L enables the D flip-flop PO02 so that the impending reset of its outputs may occur when the AN_RST_H goes high (after the clock watcher initiates a system reset). Furthermore, as the SHELF_L signal goes high, the output of the 3 input NAND gate PO16 goes low, enabling the WATCH_EN_L signal because the other inputs to NAND gate PO16 are high from its previous state. This enables the clock watcher function in the VDD comparator cell PO05 so that the absence of a clock signal CLK from the system clocks circuit 19 will cause a system reset in 0.2 mS to 2 mS. When this occurs the clock watcher output NOCLK_L goes low.

Recall that an external programmer, by resetting either the SHELF_1 signal bit in power control register A 141 or the SHELF_2 bit of power control register B 142, initiates a response in which the SHELF_H signal is reset. As the SHELF_H signal thus goes low, the OR gate PO04 allows analysis of the clock reset signal RST4CLK_L alone, which can cause a desired system reset when a RIN_L and the VDD OK L signal inputs to PO22 are set. The RIN_L signal is a system reset signal from the processor subsystem 8 of FIG. 2 (but not shown in FIG. 2), arising in response to reset signals propagated from circuit to circuit within the cardiac stimulation device 110 and originating with the RST_L signal. The SHELF_H signal going low enables the 3 input NOR gate PO20 and causes its output to go high since the RUN_L and VDD_OK_L signals are set. This enables the input to SR flip-flop PO18 so that PO18 will be set when NOCLK_L goes low.

The power on reset circuit 120 now resides in a stable "after shelf mode" state, after which a system wakeup sequence takes place. Since the clock watcher enable signal WATCH_EN_L is set and interface clocks (not shown) are disabled via the low setting of the INTFCLK_GO signal, NO_CLK_L goes low to perform the function of a clockwatcher "timeout" signal which causes SR flip-flops PO18 and PO19 to enter set states. The Q output of SR flip-flop PO19 goes high so that the output of OR gate PO04 stays high. Thus, the reset signal RST_L is not set yet. Also, the Q/ output of SR flip-flop PO18 goes low to set the NO_WATCH_L signal. This causes the output of 3 input NAND gate PO16 to go high, disabling the WATCH_EN_L signal and causing the NOCLK_L signal to go high immediately. The outputs of SR flip-flop PO19 now go to the reset state because momentarily the set input is high but the reset input is still latched low by SR flip-flop PO18. The reset clock signal RST4CLK_L is set, causing the RST_L signal to be set via OR gate PO04 and 3 input AND gate PO22, and causing the OSC_OFF_L signal to be set via inventor PO33 and NOR gate PO13, and causing a full system reset to the entire stimulator 110. The processor subsystem 9 receives the reset signal via its RST_L input (not separately shown in FIG. 2) and this will cause the processor subsystem 9 to simultaneously generate output address strobe ASTB_H, io read IORD_L, and io write IOWR_L signals (not shown) in the ICtrl bus (FIG. 2) to all be set, causing an analog reset to occur via the interface signals AN_RST_H and AN_RST_L (FIG. 8).

The AN_RST_H signal will cause B_QUIET and B_QUIETBAR to be set to arrest all current drain in the interface subsystem 9, thereby permitting proper startup conditions. The AN_RST_H signal does this by initializing the D flip-flop PO02 into its reset state, causing the RUN_L signal to go high and enabling a 3 input NAND gate PO01. This allows the I_GO_L signal to be set when the oscillator (not shown) starts running, which will occur shortly. Another consequence of RUN_L going high is that the output of 3 input NOR gate PO20 goes low, causing the Q/ output of the SR flip-flop PO18 to go high, disabling the NO_WATCH_L signal and setting the WATCH_EN_L signal via the operation of the 3 input NAND gate PO16. A further consequence of a high Q/ output of the SR flip-flop PO18 is that it brings the reset input of SR flip-flop PO19 high, enabling the set input.

The AN_RST_L signal resets the D flip-flop PO25, setting the WAKING_L and INTFCLK_GO signals high to enable the clock divider 162 of FIG. 3 and creating a valid clock input CLK to the clock watcher circuit within the VDD comparator cell PO05 when the oscillator (not shown) starts. At this time, the clock watcher function is enabled, but the oscillator (not shown) is disabled because the OSC_OFF_L signal is held low by the AN_RST_H signal acting on a NOR gate PO13. This causes another clock watcher timeout, which causes the NOCLK_L signal to again be set and, in turn, causes the clock reset signal RST4CLK_L to go high since the Q output of SR flip-flop PO19 is set. This signal ripples through the OR gate PO04 and the 3 input AND gate PO22 to carry the RST_L signal high and reset the circuits within the entire stimulator 110.

Now, the processor subsystem 8 releases the IO_WR_H and ASTB_L signals (not shown) and resets the AN_RST_H and AN_RST_L signals to cause numerous responses in the power on reset circuit 120 of FIG. 8. The B_QUIET and B_QUIETBAR signals are reset by the operation of the OR gate PO14, the level shifter PO09 and the gate drivers PO10 and PO11. The D flip-flop PO02 set and reset inputs are held high to continue to hold the RUN_L signal high until its clock input signal A_L goes high after the oscillator starts. Resetting the AN_RST_L signal causes all three inputs of the NAND gate PO01 to go high, setting the I_GO_L signal and starting an interface bias generator (not shown). Recalling that the RST_L signal is now high, its inverse, which is one of the inputs to the two input NOR gate PO13, is therefore low. Accordingly, when the AN_RST_H signal is reset, both inputs of NOR gate PO13 are low, causing OSC_OFF_L to finally go high, which starts the oscillator. At this point, the power on reset circuit 120 is in a stable state until the oscillator begins operating.

In response to starting the oscillator (not shown), the NOCLK_L signal goes high, leaving the NO_WATCH_L and RST4CLK_L signals latched in their previous high states. Starting the oscillator also causes the clock input signal A_L to make a low to high transition, which sets the RUN_L signal via the operation of the D flip-flop PO02 and resets the I_GO_L signal into its normal operating state by means of the operation of the 3 input NAND gate PO01. The RUN_L signal also causes the output of the 3 input NOR gate PO20 to go high, enabling the set input connected to the NOCLK_L signal to detect any further clock watcher responses from the VDD comparator cell PO05. Since the NO_CLK_L signal went high after the oscillator started, the set input to SR flip-flop PO18 is now held high and in its normal operating state.

This concludes the entire wakeup reset sequence. The interface subsystem 9 is ready to operate normally.

Figure 12:
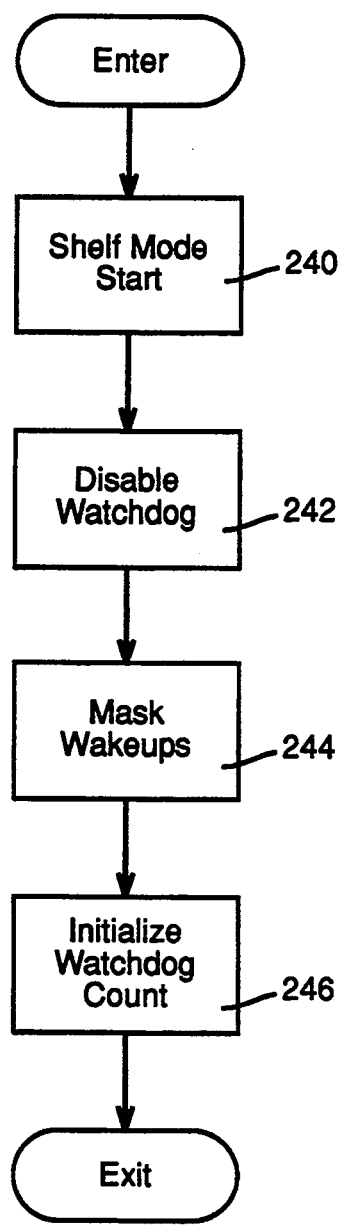
FIG. 12 is a flow chart which identifies the operations performed by an external programmer and the controller within the implantable stimulator to initiate shelf mode operation.

FIG. 12 illustrates a flow chart of a procedure for initiating shelf mode operation of the stimulator 110. An initialization and test programmer, such as an external monitoring device computer system 100 shown in FIG. 1, initiates shelf mode. In shelf-mode-start block 240, the initialization programmer 100, acting by means of telemetry block 26 (FIG. 2), first writes codes to set shelf mode bits (not shown) in power control registers A 141 and B 142 of FIG. 6, thereby setting SHELF_L and SHELF_H signals in the power supply 18 (FIGS. 2 and 5) and turning off all current sources other than those driving the oscillator (not shown) within system clocks 19 (FIG. 2).

Next, in disable-watchdog block 242, the initialization programmer 100 disables the watchdog timer 172 (FIG. 3) by setting a bit within the clock divider 162 register (FIG. 3) that, in turn, sets the SHELF signal within the test and wakeup block 150.

In mask-wakeups block 244, the initialization programmer 100 then masks all wakeups in the interface subsystem 9 and, by writing codes to the wakeup mask register 166, masks all wakeups in the processor subsystem 8 of FIG. 2, other than those wakeups that drive the telemetry block 26. Writing the wakeup mask register 166 to set each timer wakeup mask stops timer driven routines in controller 28. There are 3 timers (not shown) in timers block 27 (FIG. 2) which continuously time intervals and cause software to run upon the expiration of their timing periods. Other active wakeups, which are normally active in a pacemaker application, are a cardiac sense signal wakeup from the pace/sense analog circuit 16, a measurement done wakeup from the interface controller 15, telemetry wakeups (data sent, data received and channel closed) and a software wakeup from the controller 28. The cardiac sense signal and the measurement done signal are inactivated because they are in the interface subsystem 9 which, in shelf mode, is turned off. The software wakeup does not occur in shelf mode because it is always requested in the process of a timer, sense or measurement wakeup. The telemetry wakeups are still active in shelf mode to maintain communication between the programmer 100 and the stimulator 110.

Finally, in initialize-watchdog-count block 246, the initialization programmer 100 initializes the watchdog timer 172 (FIG. 3) by writing an appropriate key code to the watchdog timer 172 register, as was discussed previously herein. Thus, when a stimulator 110 is shipped from the factory, it can be shipped in shelf mode, which depletes much less energy from the battery before the stimulator is implanted. In this mode, the stimulator 110 only has telemetry functioning and power is supplied to the VDD supply alone.

When the stimulator 110 is implanted, which may occur after operating in shelf mode for months, shelf mode must be terminated and normal stimulator operations commenced. There are two methods for terminating shelf mode. One method, discussed immediately below, requires communication with an external programmer. A second method, discussed later, employs a removable activation pin.

Figure 14:
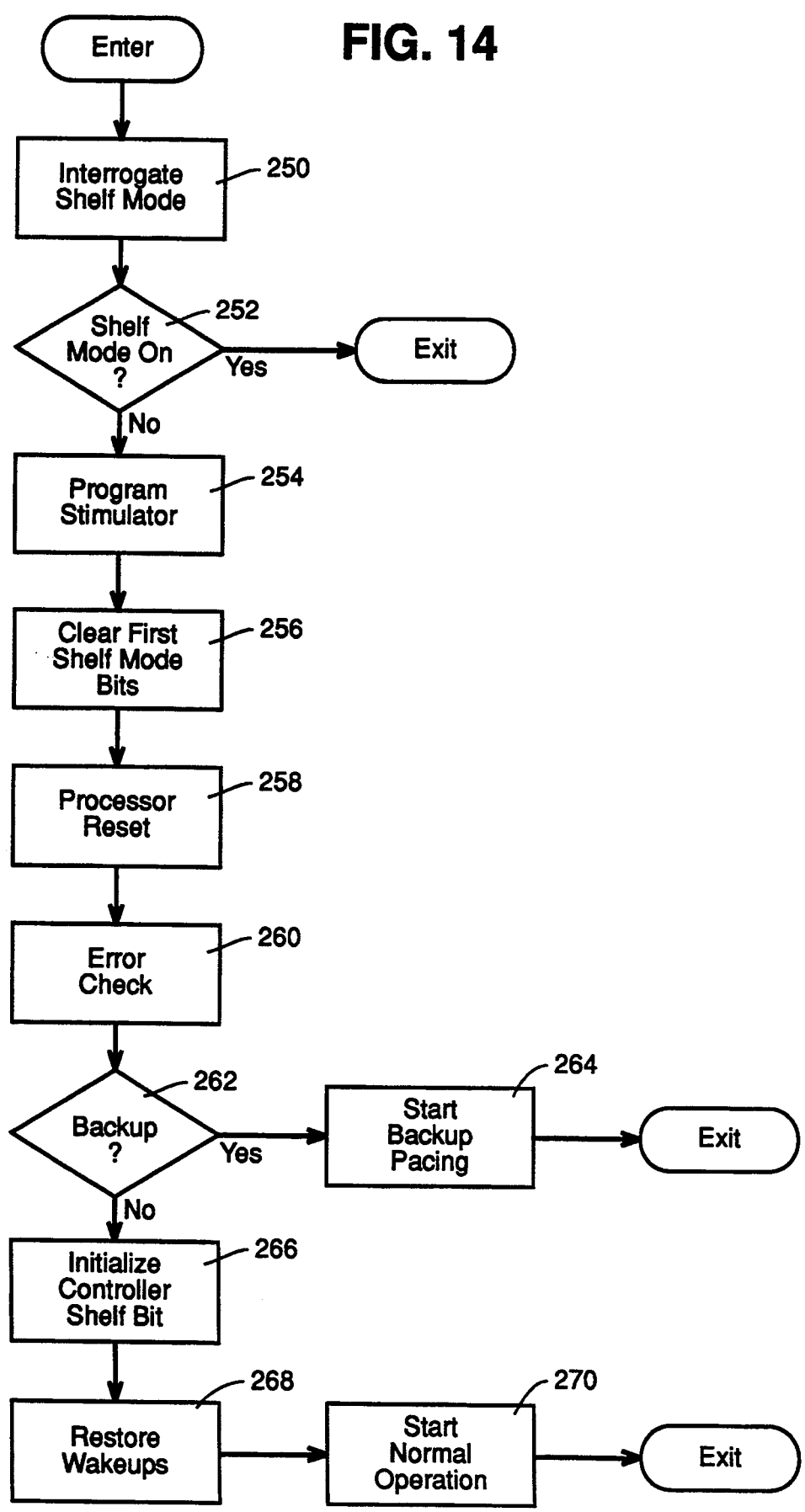
FIG. 14 is a flow chart which identifies the operations performed by an external programmer and the controller within the stimulator to terminate shelf mode operation within a stimulator.

Referring to FIG. 14, the first method for terminating shelf mode, utilizing external programmer 100, is illustrated by a flow chart. First, in interrogate-shelf-mode-block 250, the programmer reads registers within the stimulator 110 to determine whether the stimulator 110 is in shelf mode and whether any errors have occurred in stimulator 110 operations.

In shelf-mode-on?-logic block 252, the programmer 100 determines if shelf mode is in operation and, if so, programs the programmable parameters of the stimulator 110 (FIG. 1) in program-stimulator block 254. The programmer must set the stimulating parameters before writing to the shelf mode registers to terminate the mode because part of the terminating process is to reset the stimulator 110 and initialize operational parameters of the stimulator 110, which breaks the communication link between the stimulator and programmer.

In clear-first-shelf-mode-bits block 256, the programmer 100 writes 0 to shelf mode register bits, first to the shelf mode bit of the clock divider 162 register (FIG. 3) and then to the shelf mode bit of power control register B 141 (FIG. 6). The controller 28 then runs through an initialization procedure in processor-reset block 258, which breaks the telemetry link.

The controller 28 must determine whether any error conditions exist in the stimulator 110 which require it to enter an emergency mode of pacing, called backup pacing mode. In error-check block 260, the controller 28 checks for a memory failure by interrogating an error location in volatile memory of RAM/ROM 190 (FIG. 3) which designates whether the watchdog timer 172 has detected a RAM memory error. If an error occurred, the controller 28, under the control of backup? logic block 262, begins stimulator operation in backup pacing mode in start-backup-pacing block 264. Otherwise, the controller 28, while still in error-check block 260, interrogates the WAKEBIT_H signal in the power control register B 142. This WAKEBIT_H signal is set automatically by the power supply circuit 18 when the programmer 110 clears either the shelf mode bit (not shown) in power control register A 141 or power control register B 141. Assertion of the WAKEBIT_H signal (which is not cleared on system reset) will be an indicator to the controller 28 in the error check block 260 that the stimulator 110 is coming out of shelf mode. The power supply circuit 18 causes a system reset signal RST_L (FIG. 8) immediately after assertion of the WAKEBIT H signal and the processor subsystem 8 is awakened. Therefore, if WAKEBIT_H is 0, the error check block 260 determines that initialization is occurring because of an error condition such as VDD reset and under the control of the backup? logic block 262, the controller 28 branches to the start backup pacing block 264 and begins stimulator operation in backup pacing mode.

If WAKEBIT_H is 1, the error check block 260 determines that initialization is due to termination of shelf mode and the controller advances to the initialize controller shelf bit block 266 from the backup? logic block 262. At this point, the controller 28 clears the shelf bit in the clock divider 162. Although the programmer 100 has already cleared this bit, the controller 28 performs the same operation in case shelf mode is terminated using an activation pin instead of a programmer. Similarly, in restore-wakeups block 268, the controller 28 unmasks timer wakeups in case the programmer is not available to do so.

The controller 28 then, in start-normal-operation block 270, resets WAKEBIT_H of the power control register B 142 and clears the shelf mode bit of power control register A 141 to complete clearing of the three shelf mode bits. In block 270, the controller may also write information to a shelf mode information logging location in RAM/ROM 190 of the controller 28 to designate the date and time of the shelf mode wakeup if such a record is maintained by controller 28 operations.

This sequence of operations will only allow the stimulator 110 to enter a normal pacing mode if memory is valid and the stimulator 110 is leaving shelf mode. Otherwise, the reset was caused by an error condition, in which case the pacemaker will enter a backup mode. Any failure bits in memory may be reset by the programmer 110.

One problem with the method for initiating and terminating shelf mode described respectively in FIG. 12 and FIG. 14 is that a programmer 100 is required to terminate shelf mode. There is nothing to prevent a stimulator from being implanted without being programmed. It would be desirable for the stimulator to somehow sense that it had been implanted and to respond by automatically terminating shelf mode. Accordingly, a further embodiment of the invention is a stimulator 110, illustrated in FIGS. 13A, 13B and 13C, which interfaces with an activation pin 300 adapted to be inserted into the lead cavity 302 of the stimulator header 304. The activation pin 300 must be removed from the lead cavity and a stimulating lead (not shown) inserted therein for the stimulator 110 to function. The activation pin 300 is inserted into the lead cavity 302 through an opening 303 in the stimulator header 304 prior to initializing shelf mode at the factory. The lead cavity 302 has an interior end 316 and an exterior end 318 at the opening 303. The stimulator header 304 includes a conductive cylindrical TIP lead connector terminal or contact 312 and a conductive garter or canted coil spring RING lead connector terminal or contact 314 for electrically connecting a bipolar lead to electronics within the stimulator 110. The coil spring of lead connector terminal 314 is a helically wound spring element configured in a circle, thus forming a doughnut-shaped element.

Figure 13A:
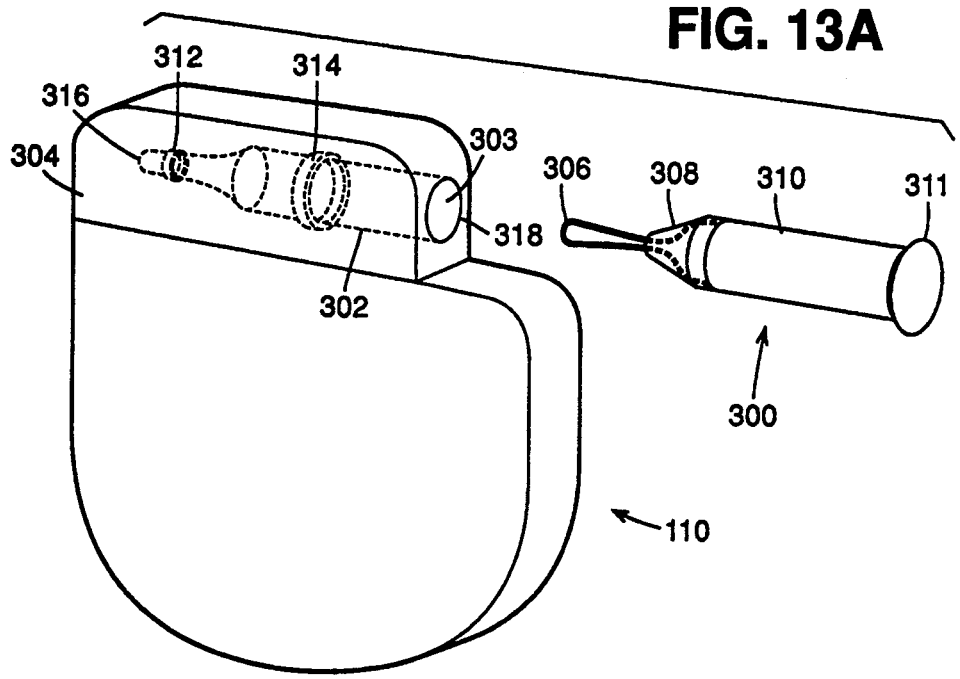
FIGS. 13A, 13B, and 13C are pictorial depictions of a stimulator employing an activation pin for terminating the shelf mode operation, illustrating the activation pin removed from the stimulator (FIG. 13A), fully inserted into the stimulator header (FIG. 13B) and removed from the stimulator header to a point at which shelf mode is terminated (FIG. 13C)
Figure 13B:
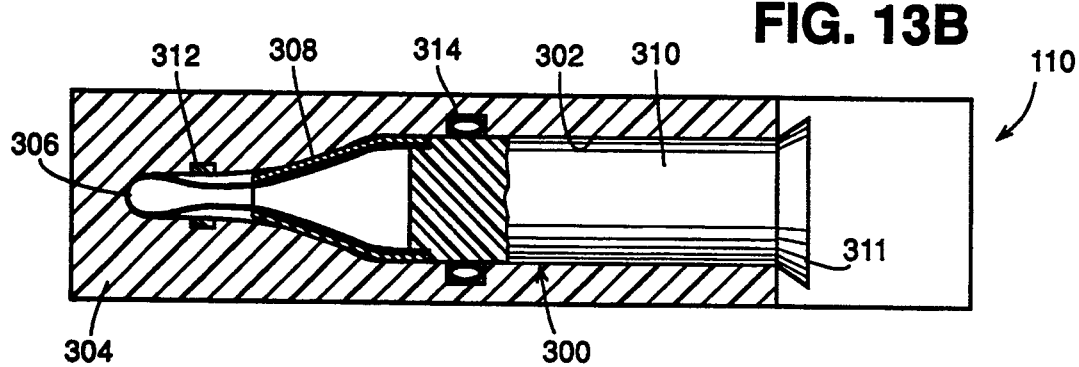
Figure 13C:
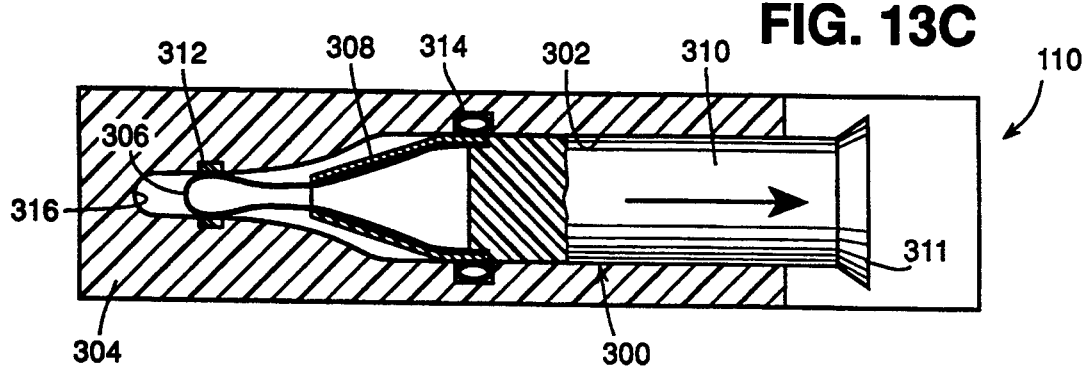

The activation pin 300 includes a conductive cathode spring portion 306 and a conductive anode tube portion 308 which are electrically connected to one another. The cathode spring 306 forms the tip of the activation pin 300, which may be inserted into the lead cavity 302. The anode tube 308 is a truncated cup-shaped element situated in the medial portion of the activation pin 300 and is constructed from electrically-conductive metal. The cathode spring 306 and anode conductive tube 308 are arranged so that, as illustrated in FIG. 13C, when the activation pin 300 is positioned in lead cavity 302 at a depth in which the cathode spring 306 is in contact with TIP lead connector terminal 312, anode terminal tube 308 will be in contact with RING lead connector terminal 314, thereby shorting the TIP and RING terminals to one another. When the activation pin 300 is positioned fully within the lead cavity 302, as shown in FIG. 13B, the cathode spring 306 does not contact the TIP lead connector terminal 312 and the anode tube 308 does not contact the RING lead connector terminal 314. On the side of the activation pin 300 away from the cathode spring portion 306, the anode tube 308 is affixed to an insulative plastic pin holder 310 which extends to a flange 311 most distal from the cathode spring 306. The flange 311 provides a gripping surface to allow easy removal of the activation pin 300 from the lead cavity 302.

Upon implantation, the activation pin 300 must be removed from the lead cavity 302 in order to permit insertion of a stimulating lead (not shown) into the cavity. When the activation pin 300 is removed (assuming shelf mode has been previously activated), the cathode spring 306 and the anode tube 308 short the TIP and RING lead connector terminals 312 and 314 together, causing shelf mode to be terminated by circuitry, illustrated in the diagram of FIG. 11, which generates a signal that automatically activates the shelf mode termination procedure.

Referring to FIG. 11, a p-channel MOSFET PP13 pulls a PIN_WAK_L signal high to VDD. The activation pin 300 of FIGS. 13A, 13B and 13C, which is not shown in FIG. 11, is inserted into the lead cavity 302 when the SHELF_H signal is low so that an n-channel MOSFET PP14 acts as a switch which is "OFF", thereby disabling the circuit between the TIP terminal and the PIN_WAK_L signal. Therefore, the PIN_WAK_L signal is not affected when the activation pin 300 is inserted and the TIP and RING signals, which correspond to the lead connector terminals 312 and 314, are shorted together. So long as shelf mode is not programmed, the activation pin 300 may be inserted or removed from the lead cavity 302 without influencing the operation of the stimulator 110.

When the stimulator 110 is programmed into shelf mode, the SHELF_H signal is set high. For purposes of the discussion of shelf mode, a switch SW1 is always closed and a switch SW2 is closed unless SHELF_H signal is high. During shelf mode, when SHELF_H is set high, the open switch SW2 prevents closing of a circuit between the TIP terminal and VSS, which would otherwise complete a circuit through an n-channel MOSFET PP14, pulling the PIN_WAK_L signal low and ultimately terminating shelf mode. As the activation pin 300 is removed, it is shifted from the "storage" position illustrated in FIG. 13B to a "transition" position shown in FIG. 13C, and an electrical connection from the cathode spring 306 to the anode tube 308 momentarily short circuits TIP (lead connector terminal 312) to RING (lead connector terminal 314), completing a circuit through the n-channel MOSFET PP14, pulling the PIN_WAK_L signal low and resetting a D flip-flop PP01, which acts as a latch. The resetting of the D flip-flop PP01 sets the SHELF_H signal high and the SHELF_L signal low to trigger the sequence of operations performed within the power-on-reset circuit 120 and discussed previously in conjunction with FIG. 8, which activates the WAKING_L signal 147 and invokes the wakeup sequence within the controller 28 in the manner previously described with respect to terminating shelf mode by means of programming in the discussion of FIG. 14. If the stimulator 110 was previously awakened by means of telemetry with a programmer, the removal of the activation pin 300 will have no effect except for momentarily shorting the lead connectors, which produces no consequences affecting the stimulator 110.

Prior to beginning the initiating shelf mode operation detailed in the discussion of FIG. 12, the activation pin 300 is inserted into the stimulator header 304, preferably as a last step in the stimulator 110 manufacturing process. The stimulator 110 is then placed in shelf mode. Later, when the stimulator 110 is to be implanted, shelf mode is terminated either by performing the procedures discussed with respect to the procedure of FIG. 14 or by merely removing the activation pin 300 from the lead cavity 302. Either shelf mode termination procedure will leave the stimulator 110 in the same active state without interfering with the other procedure so that either or both procedures may be invoked without causing any unexpected consequences.

Figure 15A:
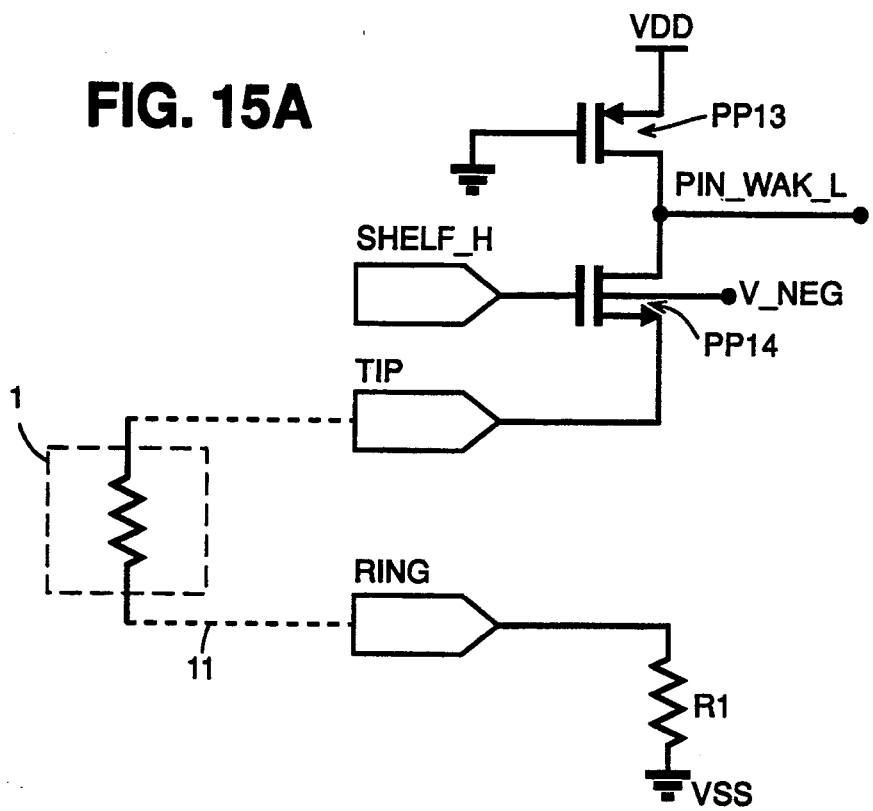
FIGS. 15A and 15B are circuit diagrams which illustrate partial equivalent circuits of the power control register B of FIG. 11 when a bipolar lead and a unipolar lead, respectively, are attached to the stimulator and shelf mode is activated.
Figure 15B:
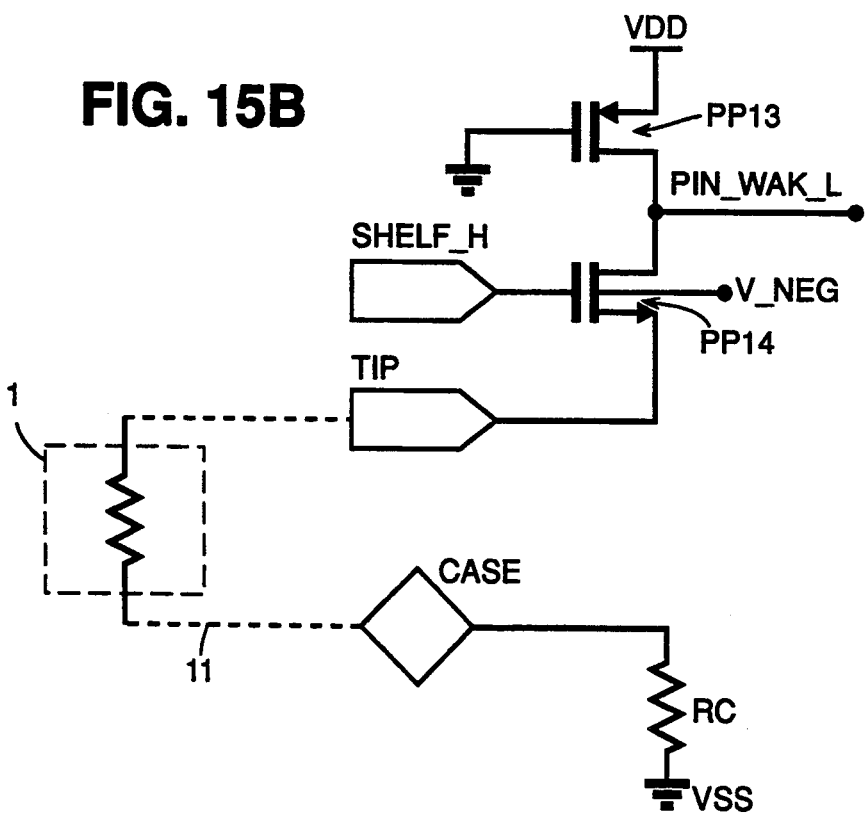

It may be desirable to provide an embodiment of the invention for terminating shelf mode that does not require the use of an activation pin 300. The circuitry within the power control register B 142 of FIG. 11 supports this further embodiment of the invention without modification. Shelf mode may be initialized in the factory without inserting an activation pin into the lead cavity of the stimulator. Referring to FIGS. 1, 11 and 13A–13C, when the stimulator is implanted a stimulation lead 11 (FIG. 1) is implanted into the heart 1 and inserted into the lead cavity 302 (FIG. 13A). When shelf mode is activated, switch SW1 (FIG. 11) is closed and switch SW2 is open in the manner previously described. Thus, the shelf mode switch circuitry within the power control register B 142, shown in FIG. 11, takes the form of the equivalent circuits shown in FIGS. 15A and 15B. All that is required to terminate shelf mode and to activate the stimulator is for the TIP lead connector to be electrically connected to ground. This is accomplished using a bipolar lead 11, as shown in FIG. 15A, in which the TIP lead connector terminal is connected to the RING lead connector terminal through the heart 1. As previously disclosed herein, an activation pin was used to make this electrical connection. However, if no activation pin is employed, the same electrical connection may be provided by the stimulation lead 11 and the heart 1. The lead 11 is standard in the art of cardiac pacemakers and includes a ring electrode, a tip electrode and conductors attached to each electrode and running the length of the lead to a connector which is inserted into the lead cavity 302 and makes a connection with the TIP and RING connector terminals, respectively. (None of the elements within the lead are shown.) When the lead 11 is implanted within the heart 1, the heart makes an electrical connection between the TIP and the RING connector terminals (with a tissue impedance of approximately 500 ohms). When the lead 11 connector is inserted into the lead cavity 302, this electrical connection completes a circuit through the n-channel MOSFET PP14, pulling the PIN_WAK_L signal low and terminating shelf mode, as was disclosed hereinbefore. Similarly, if a unipolar lead is attached to the stimulator, as shown in FIG. 15B, the TIP connector terminal is electrically connected through the patient's heart 1 to a CASE connector, which is outside the circuit of the power control register B 142 shown in FIG. 11, but which is also connected to the ground reference of the stimulator circuit through a resistor RC.

From the foregoing discussion, it is apparent that the present invention provides an apparatus and method for placing an implantable stimulator in a quiescent state during the time between manufacture and implantation. In this quiescent state, the stimulator maintains communication capabilities to allow its subsequent activation. The capability of entering a quiescent state significantly extends the battery life of the stimulator or allows the size of the stimulator to be reduced. The stimulator may be activated by a programmer, or automatically, without the need for an activating programmer, prior to implantation, by the removal of an activation pin that has been inserted into the lead cavity. The termination pin prevents the implantation of a deactivated stimulator. Further, the insertion into the stimulator of the connector end of an implanted unipolar or bipolar stimulation lead will also cause activation of the stimulator.

Although the invention has been shown and described with reference to particular embodiments, it is to be understood that these embodiments are merely illustrative of the application of the principles of the invention. Numerous modifications may be made therein and other arrangements may be devised without departing from the true spirit and scope of the invention.

What is claimed is:

1. A method of selectively controlling an implantable stimulator having stimulator circuits which operate either in a quiescent state of operation or in an active state of operation, in response to commands from an external communicating device, said stimulator having an oscillator providing timing signals for use in switching from one of said states of operation to another of said states of operation and telemetry circuitry for communicating with the external communicating device, said method comprising the steps of:

transmitting a deactivating command from said external communicating device to said implantable stimulator;

generally disabling power to substantially all of said stimulator circuits except said oscillator and said telemetry circuitry in response to said deactivating command;

generally providing disabling signals to substantially all of said stimulator circuits except said oscillator and said telemetry circuitry while continuing to enable said quiescent state of operations in response to said deactivating command;

subsequently transmitting an activating command from an external communicating device to said implantable stimulator;

providing enabling signals to said disabled stimulator circuits in response to said activating command; and enabling power to said power-disabled stimulator circuits in response to said activating command so as to enable said active state of operation of said stimulator.

2. A method in accordance with claim 1, wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, and a low-rate timer for activating said error mode of stimulator operation in the event that the stimulator fails to conclude a cardiac cycle by the occurrence of the first of two events, pacing the heart and sensing of a natural cardiac depolarization, within a predetermined time interval following said activating command, said method further comprising the steps of:

disabling said low rate timer in response to said deactivating command; and enabling said low rate timer in response to said activation command.

3. A method in accordance with claim 2, wherein said error detection circuitry includes at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

4. A method in accordance with claim 1 wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, said error detection circuitry including at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

5. A method of selectively controlling an implantable stimulator having an activation pin and having stimulator circuits which operate either in a quiescent state of operation in response to a command from an external communicating device or in an active state of operation in response to removal of said activation pin, said stimulator having an oscillator providing timing signals for use in switching from one of said states of operation to another of said states of operation, an aperture configured to accept one or another of a stimulation lead and said activation pin, and a circuit means to detect removal of an inserted activation pin, and said stimulator having telemetry circuitry means for communicating with the external communicating device, said method comprising the steps of:

transmitting a deactivating command from said external communicating device to said implantable stimulator;

generally disabling power to substantially all of said stimulator circuits except said oscillator and said telemetry circuitry in response to said deactivating command;

generally providing disabling signals to substantially all of said stimulator circuits except said oscillator and said telemetry circuitry while continuing to enable said quiescent state of operation, in response to said deactivating command;

inserting said activation pin into said stimulator aperture;

subsequently removing said activation pin from said stimulator aperture;

providing enabling signals to said disabled stimulator circuits in response to the removal of said activation pin; and enabling power to said disabled stimulator circuits in response to the removal of said activation pin.

6. A method in accordance with claim 5, wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, and a low-rate timer for activating said error mode of stimulator operation in the event that the stimulator fails to conclude a cardiac cycle by the occurrence of the first of two events, pacing the heart and sensing of a natural cardiac depolarization, within a predetermined time interval following the removal of said activation pin, said method further comprising the steps of:

disabling said low rate timer in response to said deactivating command; and enabling said low rate timer in response to the removal of said activation pin.

7. A method in accordance with claim 6, wherein said error detection circuitry includes at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

8. A method in accordance with claim 5, wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, said error detection circuitry including at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

9. A method of selectively controlling an implantable programmable stimulator having stimulator circuits therein to operate either in a quiescent state or in an active state in response to external commands from an external communicating device, said stimulator including a communication circuit means for communicating with the external communicating device, at least one storage register, a power supply means for providing current sources to said stimulator circuits, an oscillator for providing timing signals to said stimulator circuits, and a wakeup circuit means for notifying the stimulator of internal and external wakeup events, such wakeup events being individually enabled and disabled, said method comprising the steps of:

transmitting a deactivating command from said external communicating device to said implantable stimulator;

forming a signal corresponding to said transmitted deactivating command and storing said signal in said at least one storage register;

controlling said power supply means to generally disable said current sources to substantially all of said stimulator circuits except said oscillator and said communication circuit means in response to said deactivating command;

controlling said wakeup circuit means to generally disable wakeup events while continuing to enable the wakeup events associated with said communication circuit means in response to said deactivating command;

subsequently interrogating said storage register to determine whether said stimulator is in a deactivated state;

programming said deactivated stimulator;

transmitting an activating command from an external communicating device to said deactivated stimulator;

controlling said wakeup circuit means to enable wakeup events in response to said activating command; and controlling said power supply means to provide said current sources to said disabled stimulator circuits in response to said activating command.

10. A method in accordance with claim 9, wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, and a low-rate timer for activating said error mode of stimulator operation in the event that the stimulator fails to conclude a cardiac cycle by the occurrence of the first of two events, pacing the heart and sensing of a natural cardiac depolarization, within a predetermined time interval following said activating command, said method further comprising the steps of:

disabling said low rate timer in response to said deactivating command; and enabling said low rate timer in response to said activation command.

11. A method in accordance with claim 10, wherein said error detection circuitry includes at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

12. A method in accordance with claim 9 wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, said error detection circuitry including at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

13. A method of selectively controlling an implantable programmable stimulator having an activation pin and having stimulator circuits which operate either in a quiescent state in response to a command from an external communicating device or in an active state in response to removal of said activation pin, said stimulator including an aperture configured to accept one or another of a stimulation lead and said activation pin, a pin removal circuit means to detect removal of an inserted activation pin, a communication circuit means for communicating with the external communicating device, at least one storage register, a power supply means for providing current sources to said stimulator circuits, an oscillator for providing timing signals to said stimulator circuits, and a wakeup circuit means for notifying the stimulator of internal and external wakeup events, such wakeup events being individually enabled and disabled, said method comprising the steps of:

transmitting a deactivating command from said external communicating device to said implantable stimulator;

forming a signal corresponding to said transmitted deactivating command and storing said signal in said at least one storage register;

controlling said power supply means to generally disable said current sources to substantially all of said stimulator circuits except said oscillator and said communication circuit means in response to said deactivating command;

controlling said wakeup circuit means to generally disable wakeup events while continuing to enable the wakeup events associated with said communication circuits means in response to said deactivating commands;

inserting said activation pin into said stimulator aperture;

subsequently removing said activation pin from said stimulator aperture;

controlling said wakeup circuit means to enable wakeup events in response to the removal of said activation pin; and controlling said power supply means to provide current sources to said disabled stimulator circuits in response to the removal of said activation pin.

14. A method in accordance with claim 13, wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, and a low rate timer for activating said error mode of stimulator operation in the event that the stimulator fails to conclude a cardiac cycle by the occurrence of the first of two events, pacing the heart and sensing of a natural cardiac depolarization, within a predetermined time interval following the removal of said activation pin, said method further comprising the steps of:

disabling said low rate timer in response to said deactivating command; and enabling said low rate timer in response to the removal of said activation pin.

15. A method in accordance with claim 14, wherein said error detection circuitry includes at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

16. A method in accordance with claim 13, wherein said stimulator includes sensing circuitry for sensing natural cardiac depolarizations of a patient's heart, pacing circuitry for providing pacing pulses to the patient's heart, error detection circuitry for establishing an error mode of operation of said stimulator in which pacing pulses are generated and delivered to the heart, said error detection circuitry including at least one error detection circuit for detecting whether at least one predetermined error condition exists, said method comprising the steps of:

responsive to said activating command transmitting step, detecting whether said at least one error condition is extant in the stimulator; and activating said error mode of stimulator operation in response to the detection of such error condition.

17. An implantable stimulator having stimulator circuits which operate either in a quiescent state of operation or an active state of operation in response to commands from an external communicating device, said stimulator comprising:

a power source for providing Dower to said stimulator circuits;

an oscillator for providing timing signals for use in switching from one of said states of operation to another of said states of operation;

telemetry means for communicating with the external communicating device;

means responsive to a deactivating command received by said telemetry means for generally disabling power to substantially all of said stimulator circuits except said oscillator and said telemetry means;

means responsive to said deactivating command for generally providing disabling signals to substantially all of said stimulator circuits except said oscillator and said telemetry means to enable said quiescent state of operations;

means responsive to an activating command received by said telemetry means for enabling said active state of operations of said stimulator; and means responsive to said activating command for providing enabling power to said disabled stimulator circuits.

18. A stimulator in accordance with claim 17, further comprising;

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart;

a low rate timer for activating said error mode of stimulator operation when the stimulator fails to conclude a cardiac cycle by the occurrence of the first of two events, pacing the heart and sensing of a natural cardiac depolarization, within a predetermined time interval following said activating command;

means responsive to said deactivating command for disabling said low rate timer; and means responsive to said activating command for enabling said low rate timer.

19. A stimulator in accordance with claim 18, wherein said error detection means includes at least one error detection circuit for detecting whether at least one predetermined error condition exists, said stimulator further comprising:

means responsive to said activating command for detecting whether said at least one error condition is extant in the stimulator; and means responsive to the detection of such error condition for activating said error mode of stimulator operation.

20. A stimulator in accordance with claim 17, further comprising:

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart, said error detection means including at least one error detection circuit for detecting whether at least one predetermined error condition exists;

means responsive to said activating command for detecting whether said error condition is extant in the stimulator; and means responsive to the detection of such error condition for activating said error mode of stimulator operation.

21. An implantable stimulator having stimulator circuits operable either in a quiescent state of operation in response to a command from an external communicating device or in an active state of operation in response to removal of an inserted activation pin, said stimulator comprising:

a power source for providing power to said stimulator circuits;

an oscillator for providing timing signals to said stimulator circuits for use in switching from one of said states of operation to another of said states of operation;

an aperture in said stimulator for receiving said inserted activation pin and for accepting a stimulation lead upon removal of said inserted activation pin;

circuit means for detecting removal of said inserted activation pin;

telemetry means for communicating with the external communicating device;

means responsive to a deactivating command received by said telemetry means for generally disabling power to substantially all of said stimulator circuits except said oscillator and said telemetry means;

means responsive to said deactivating command for generally providing disabling signals to substantially all of said stimulator circuits except said oscillator and said telemetry means;

means for detecting removal of said activation pin from said stimulator aperture;

means responsive to the detection of the removal of said activation pin for providing enabling signals to all of said disabled stimulator circuits; and means responsive to the detection of the removal of said activation pin for enabling power to all of said disabled stimulator circuits.

22. A stimulator in accordance with claim 21, further comprising;

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart;

a low rate timer for activating said error mode of stimulator operation when the stimulator fails to conclude a cardiac cycle by the occurrence of the first of two events, pacing the heart and sensing of a natural cardiac depolarization, within a predetermined time interval following said activating command;

means responsive to said deactivating command for disabling said low rate timer; and means responsive to said detection of the removal of said activation pin for enabling said low rate timer.

23. A stimulator in accordance with claim 22, wherein said error detection means includes at least one error detection circuit for detecting whether at least one predetermined error condition exists, said stimulator further comprising:

means responsive to the removal of said activation pin for detecting whether said at least one error condition is extant in the stimulator; and means responsive to the detection of such error condition for activating said error mode of stimulator operation.

24. A stimulator in accordance with claim 21, further comprising:

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart, said error detection means including at least one error detection circuit for detecting whether at least one predetermined error condition exists;

means responsive to the removal of said activation pin for detecting whether said at least one error condition is extant in the stimulator; and means responsive to the detection of such error condition for activating said error mode of stimulator operation.

25. An implantable stimulator having stimulator circuits which operate either in a quiescent state of operation or an active state of operation in response to commands from an external communicating device, said stimulator comprising:

telemetry means for communication with the external communicating device;

at least one storage register;

a power supply for supplying and regulating current sources to said stimulator circuits;

an oscillator for providing timing signals to said stimulator circuits for use in switching from one of said states of operation to another of said states of operation;

a wakeup circuit means for notifying the stimulator of internal and external wakeup events;

means for storing a representation of a deactivating command received by said telemetry means in a deactivating command storage register of said at least one storage register;

means responsive to said deactivating command received by said telemetry means for controlling said power supply to generally disable current sources to substantially all of said stimulator circuits except said oscillator and said telemetry means;

means responsive to said deactivating command for controlling said wakeup circuit means to generally disable wakeup events while continuing to enable those wakeup events associated with said telemetry means;

means for interrogating said deactivating command storage register to determine whether said stimulator is in a deactivated state;

means for programming said deactivated stimulator;

means responsive to an activating command received by said telemetry means for controlling said wakeup circuit means to enable wakeup events in response to said activating command; and means responsive to said activating command for controlling said power supply to enable current sources to said disabled stimulator circuits.

26. A stimulator in accordance with claim 25, further comprising:

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart;

a low rate timer for activating said error mode of stimulator operation when the stimulator fails to conclude a cardiac cycle by the occurrence of the first of two events, pacing the heart and sensing of a natural cardiac depolarization, within a predetermined time interval following said activating command;

means responsive to said deactivating command for disabling said low rate timer; and means responsive to said activating command for enabling said low rate timer.

27. A stimulator in accordance with claim 26, wherein said error detection means includes at least one error detection circuit for detecting whether at least one predetermined error condition exists, said stimulator further comprising:

means responsive to said activating command for detecting whether said at least one error condition is extant in the stimulator; and means responsive to the detection of such error condition for activating said error mode of stimulator operation.

28. A stimulator in accordance with claim 25, further comprising:

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart, said error detection means including at least one error detection circuit for detecting whether at least one predetermined error condition exists;

means responsive to said activating command for detecting whether said error condition is extant in the stimulator; and means responsive to the detection of such error condition for activating said error mode of stimulator operation.

29. An implantable stimulator having stimulator circuits which operate either in a quiescent state of operation in response to a command from an external communicating device or in an active state of operation in response to removal of an inserted activation pin, comprising:

telemetry means for communicating with the external communicating device;

an aperture in said stimulator for receiving said inserted activation pin and for accepting a stimulation lead upon removal of said inserted activation pin;

circuit means for detecting removal of said inserted activation pin;

at least one storage register;

a power supply for supplying and regulating current sources to said stimulator circuits;

an oscillator for providing timing signals to said stimulator circuits for use in switching from one of said states of operation to another of said states of operation;

a wakeup circuit means for notifying the stimulator of internal and external wakeup events;

means for storing a representation of a deactivating command received by said telemetry means in a deactivating command storage register of said at least one storage register;

means responsive to said deactivating command received by said telemetry means for controlling said power supply to generally disable current sources to substantially all of said stimulator circuits except said oscillator and said telemetry means;

means responsive to said deactivating command for controlling said wakeup circuit means to generally disable wakeup events while continuing to enable wakeup events associated with said telemetry means;

means for detecting removal of said activation pin from said stimulator aperture;

means responsive to the detection of the removal of said activation pin for controlling said wakeup circuit means to enable wakeup events; and means responsive to the detection of the removal of said activation pin for controlling said power supply to enable current sources to said disabled stimulator circuits.

30. A stimulator in accordance with claim 29, further comprising;

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart;

a low rate timer for activating said error mode of stimulator operation when the stimulator fails to conclude a cardiac cycle by the occurrence of the first of two events, pacing the heart and sensing of a natural cardiac depolarization, within a predetermined time interval following said activating command;

means responsive to said deactivating command for disabling said low rate timer; and means responsive to said detection of the removal of said activation pin for enabling said low rate timer.

31. A stimulator in accordance with claim 30, wherein said error detection means includes at least one error detection circuit for detecting whether at least one predetermined error condition exists, said stimulator further comprising:

means responsive to the removal of said activation pin for detecting whether said at least one error condition is extant in the stimulator; and means responsive to the detection of such error condition for activating said error mode of stimulator operation.

32. A stimulator in accordance with claim 29, further comprising:

sensing means for sensing natural cardiac depolarizations of a patient's heart;

pacing means for providing pacing pulses to the patient's heart;

error detection means for establishing an error mode of operation of said stimulator in which pacing pulses are generated and delivered to the heart, said error detection means including at least one error detection circuit for detecting whether at least one predetermined error condition exists;

means responsive to the removal of said activation pin for detecting whether said at least one error condition is extant in the stimulator; and means responsive to the detection of such error condition for activating said error mode of stimulator operation.

33. An implantable stimulator having stimulator circuits which operate either in a quiescent state of operation or an active state of operation in response to commands from an external communicating device, said stimulator comprising:

a power source for providing power to said stimulator circuits;

an oscillator for providing timing signals for use in switching from one of said states of operation to another of said states of operation;

telemetry means for communicating with the external communicating device;

means responsive to a deactivating command received by said telemetry means for generally disabling power to substantially all of said stimulator circuits except said oscillator and said telemetry means and for generally disabling signals to substantially all of said stimulator circuits except said oscillator and said telemetry means while continuing to enable stimulator operations associated with said telemetry means; and means responsive to an activating command received by said telemetry means for enabling operations of said stimulator and for enabling power to said disabled stimulator circuits.

34. An implantable stimulator having stimulator circuits which operate either in a quiescent state of operation in response to a command from an external communicating device or in an active state of operation in response to removal of an inserted activation pin, said stimulator comprising:

a power source for providing power to said stimulator circuits;

an oscillator for providing timing signals to said stimulator circuits for use in switching from one of said states of operation to another of said states of operation;

an aperture in said stimulator for receiving said inserted activation pin and for accepting a stimulation lead upon removal of said inserted activation pin;

telemetry means for communicating with the external communicating device;

means responsive to a deactivating command received by said telemetry means for generally disabling power to substantially all of said stimulator circuits except said oscillator and said telemetry means and for generally disabling signals to substantially all of said stimulator circuits except said oscillator and said telemetry means while continuing to enable stimulator operations associated with said telemetry means;

means for detecting removal of said activation pin from said stimulator aperture; and means responsive to the detection of the removal of said activating pin for providing enabling signals to said disabled stimulator circuits and for enabling power to said disabled stimulator circuits.

35. An implantable stimulator having stimulator circuits which operate either in a quiescent state of operation in response to a command from an external communicating device or in an active state of operation in response to insertion of a stimulation lead, said stimulator comprising:

a power source for providing power to said stimulator circuits;

an oscillator for providing timing signals to said stimulator circuits for use in switching from one of said states of operation to another of said states of operation;

telemetry means for communicating with the external communicating device;

means responsive to a deactivating command received by said telemetry means for generally disabling power to substantially all of said stimulator circuits except said oscillator and said telemetry means and for generally disabling signals to substantially all of said stimulator circuits except said oscillator and said telemetry means while continuing to enable stimulator operations associated with said telemetry means;

an aperture in said stimulator for receiving said stimulation lead;

circuit means for detecting insertion of said stimulation lead into said aperture; and means responsive to the detection of the insertion of said stimulation lead for providing enabling signals to said disabled stimulator circuits and for providing enabling power to said disabled stimulator circuits.

* * * * *